Figure 6:
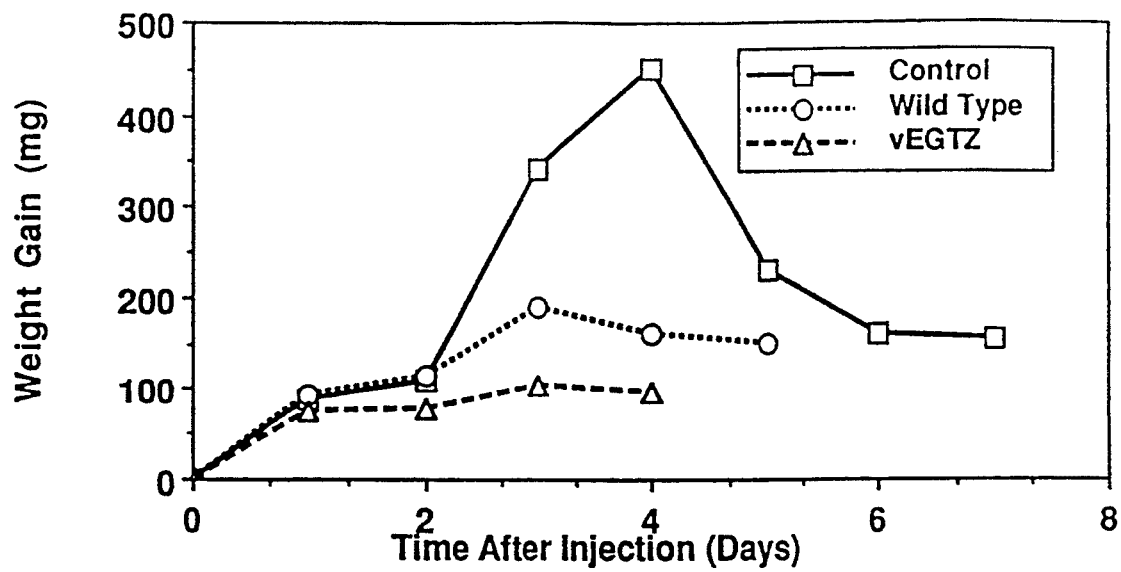

United States Patent [19]
Miller et al.

[11] Patent Number: 5,352,451
[45] Date of Patent: * Oct. 4, 1994

[54] BIOLOGICAL INSECT CONTROL AGENTS AND METHODS OF USE

[75] Inventors: Lois K. Miller; David R. O'Reilly, both of Athens, Ga.

[73] Assignee: University of Georgia Research Foundation, Inc., Athens, Ga.

[*] Notice: The portion of the term of this patent subsequent to Jan. 19, 2009 has been disclaimed.

[21] Appl. No.: 656,179

[22] PCT Filed: Jun. 29, 1990

[86] PCT No.: PCT/US90/03758

§ 371 Date: Feb. 28, 1991

§ 102(e) Date: Feb. 28, 1991

Related U.S. Application Data

[63] Continuation-in-part of Ser. No. 373,952, Jun. 29, 1989, Pat. No. 5,180,581.

[51] Int. Cl.$^5$ .................... A01N 63/00; C12N 7/01; C12N 15/00
[52] U.S. Cl. ................. 424/93.2; 435/172.1; 435/172.3; 435/235.1; 935/64
[58] Field of Search ............ 424/93 A, 93 T; 435/172.1, 172.3, 235.1, 237, 320.1; 935/32, 57, 59, 64

[56] References Cited

PUBLICATIONS

O'Reilly, D. R. et al. 1992 *Insect Biochen. Molec. Biol.* vol. 22 pp. 313–320.
Smith, G. E. et al. 1982. *Virology* vol. 123 pp. 393–406.
Dougherty et al. (1987) Physiol. Entomol. 12:23–30.
O'Reilly, D. R. & Miller, L. K. (1990) "Regulation of Expression of a Baculovirus Ecdysteroid UDPglucosyltransferase Gene" J. Virol. 64(3):1321–1328.
O'Reilly & Miller (1989) "A Baculovirus Blocks Insect Molting by Producing Ecdysteroid UDP-glucosyltransferase" Science 245:1110–1112.
Lee & Miller (1978) "Isolation of Genotypic Variants of *Autographa californica* Nuclear Polyhedrosis Virus" J. Virol. 27(3):754–767.
Kumar & Miller (1987) "Effects of Serial Passage of *Autographa californica* Nuclear Polyhedrosis Virus in Cell Culture" Virus Res. 7:335–349.
Hammock, B. D. et al. (1990) "Expression and Effects of the Juvenile Hormone Esterase in a Baculovirus Vector" Nature 344:458–461.
Hanzlik, T. N. et al. (1989) "Isolation and Sequencing of cDNA Clones Coding for Juvenile Hormone Esterase from *Heliothis virescens*" J. Biol. Chem. 264:12419–12425.
Horodyski, F. M. et al. (1989) "Isolation Expression of the Eclosion Hormone Gene From the Tobacco Hornworm, *Manduca sexta*" Proc. Natl. Acad. Sci. USA 86:8123–8127.
Kawakami, A. et al. (1990) "Molecular Cloning of the *Bombyx mori* Prothoracicotropic Hormone" Science 247:1333–1335.

(List continued on next page.)

*Primary Examiner*—Richard A. Schwartz
*Assistant Examiner*—Mary E. Mosher
*Attorney, Agent, or Firm*—Greenlee and Winner

[57] ABSTRACT

Insect control agents comprising genes encoding proteins affecting the growth, development or behavior of an insect are provided. The gene is either activated to prevent insect molting and pupation or is inactivated to reduce the feeding behavior, inhibit growth and result in the earlier death of the insect host. Such an insect control agent is exemplified by a baculovirus in which the gene encoding ecdysteriod glucosyltransferase has been inactivated. Additionally, such baculoviruses may be further modified to express a protein which affects ecdysis. Methods for producing the insect control agent and methods of controlling insects by exposing them to the insect control agent are also included.

8 Claims, 8 Drawing Sheets

OTHER PUBLICATIONS

Miller, D. W. et al. (1986) "An Insect Baculovirus Host-Vector System for High-Level Expression of Foreign Genes" Genetic Engineering, Principles & Methods, 8:277-298.

Ooi, B. G. et al. (1989) "Downstream Sequences Augment Transcription from the Essential Initiation Site of a Baculovirus Polyhedrin Gene" J. Mol. Biol. 210:721-736.

Rankin, C. et al. (1988) "Eight Base Pairs Encompassing the Transcriptional Start Point Are the Major Determinant for Baculovirus Polyhedrin Gene Expression" Gene 70:39-49.

Guarino & Summers (1988) "Functional Mapping of *Autographa california* Nuclear Polyhedrosis Virus Genes Required for Late Gene Expression" J. Virol. 62:463-471.

Steel & Davey (1985) "Integration in the Insect Endocrine System" in *Comprehensive Insect Physiology Biochemistry & Pharmacology*, Kercut and Gilbert (eds.), vol. 8, pp. 1-35.

Koolman and Karlson (1985) "Regulation of Ecdysteroid Titer: Degradation" in *Comprehensive Insect Physiology and Biochemistry and Pharmacology*, Kercut and Gilbert (eds.), vol. 7, pp. 343-361.

Miller, L. K. et al. (1983) "Bacterial, Viral, and Fungal Insecticides" Science 219:715-721.

Kirschbaum, J. B. (1985) "Potential Implication of Genetic Engineering and Other Biotechnologies to Insect Control" Ann. Rev. Entomol. 30:51-70.

Miller, L. K. (1987) "Expression of Foreign Genes in Insect Cells" in *Biotechnology In Invertebrate Pathology and Cell Culture*, Maramorosch, K. (ed.), pp. 295-303.

Miller and Dawes (1979) "Physical Map of the DNA Genome of *Autographa californica* Nuclear Polyhedrosis Virus" J. Virol. 29:1044-1055.

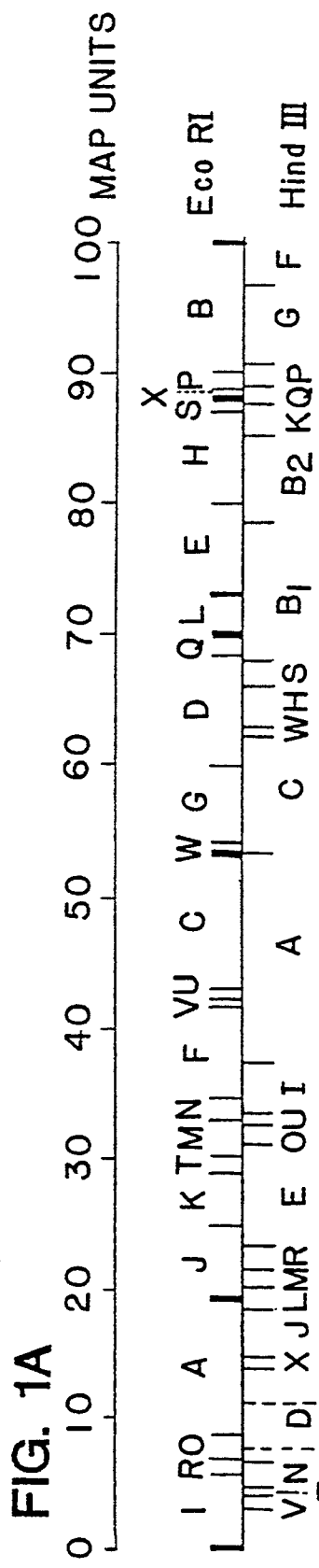
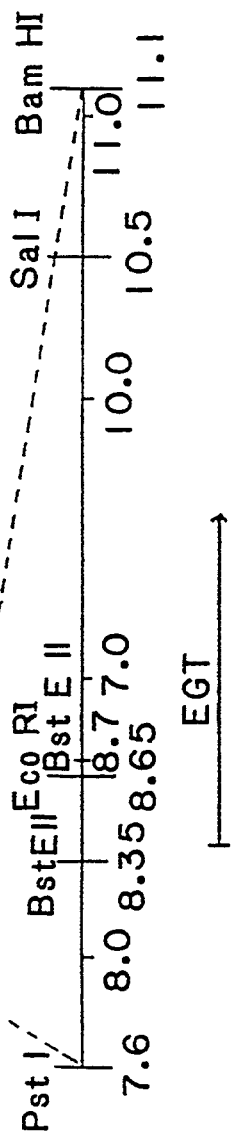
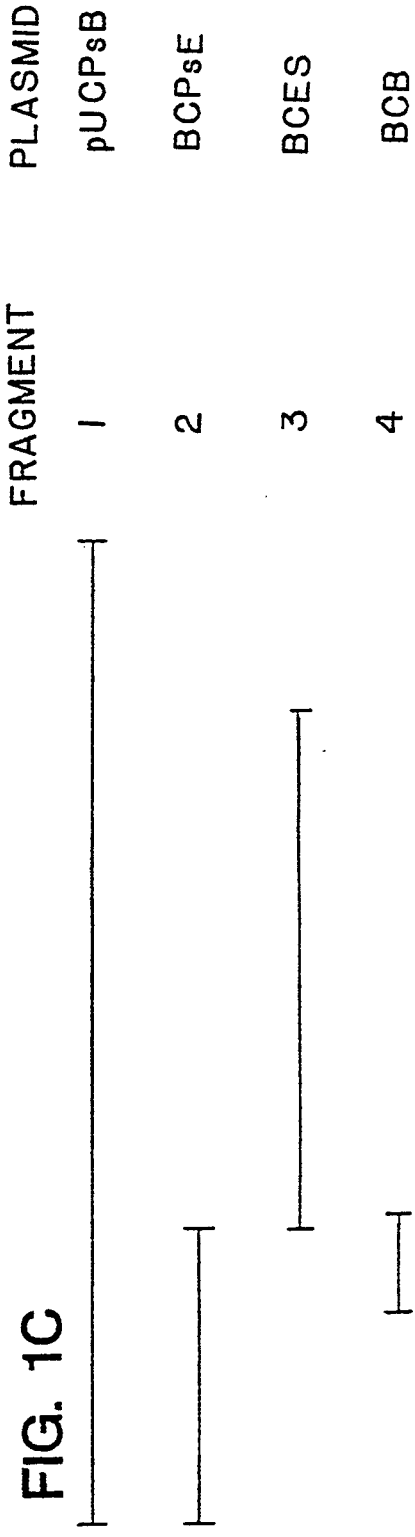

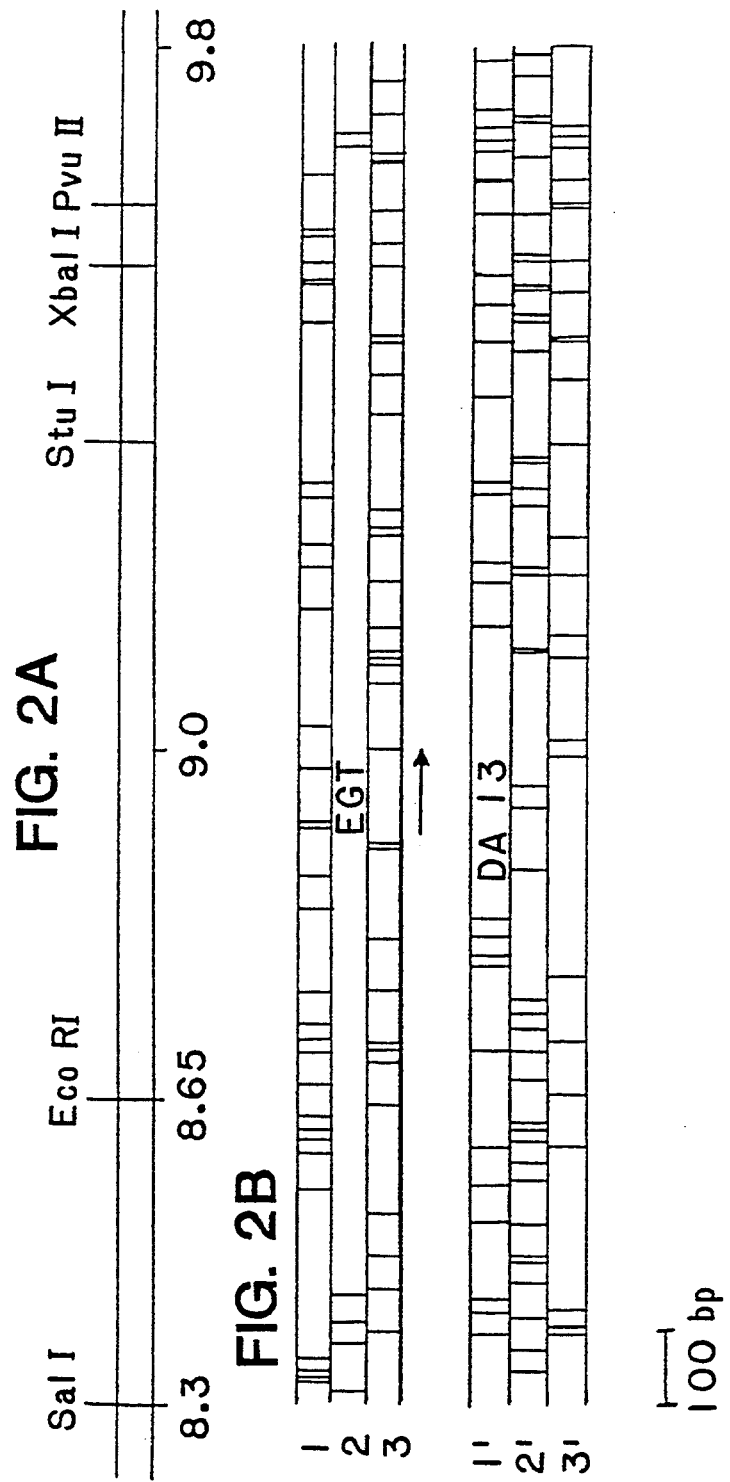

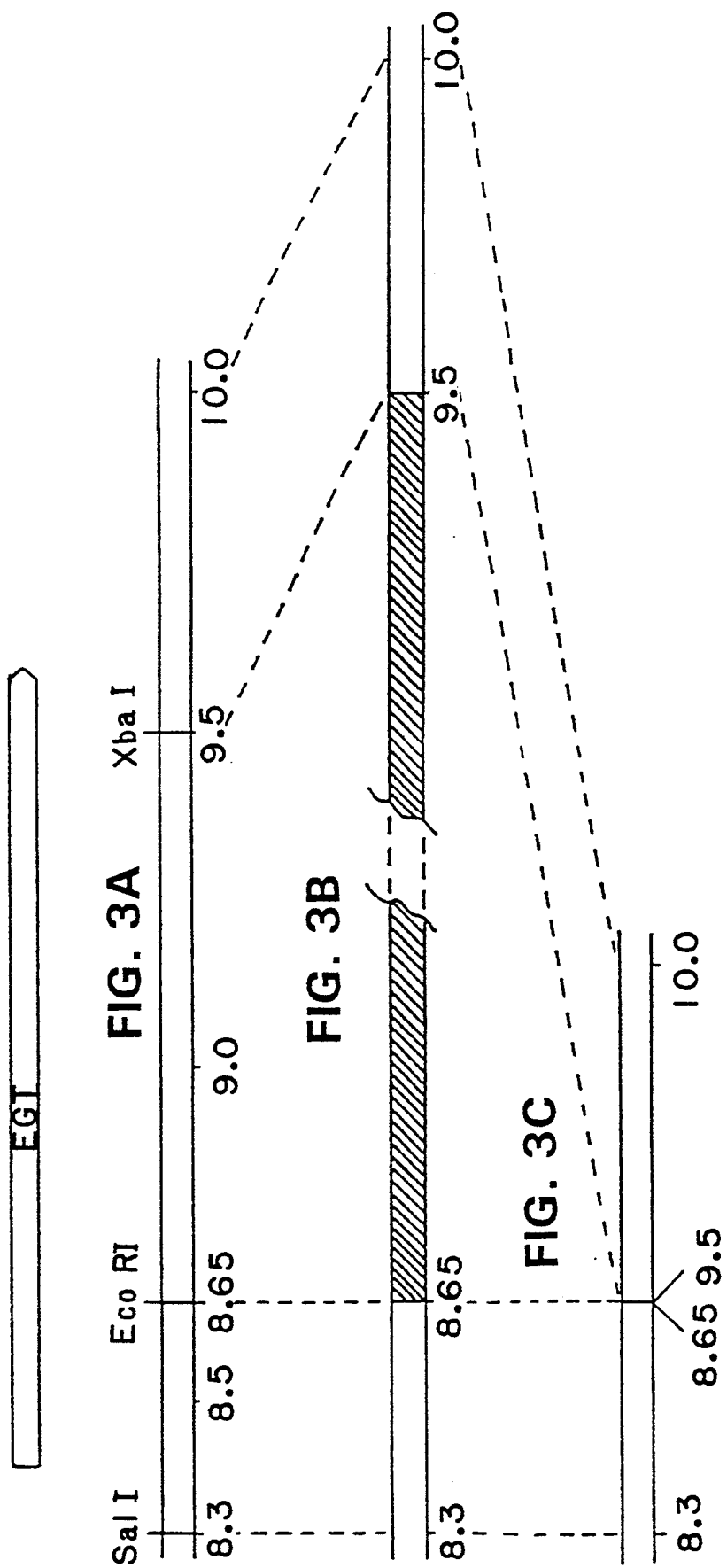

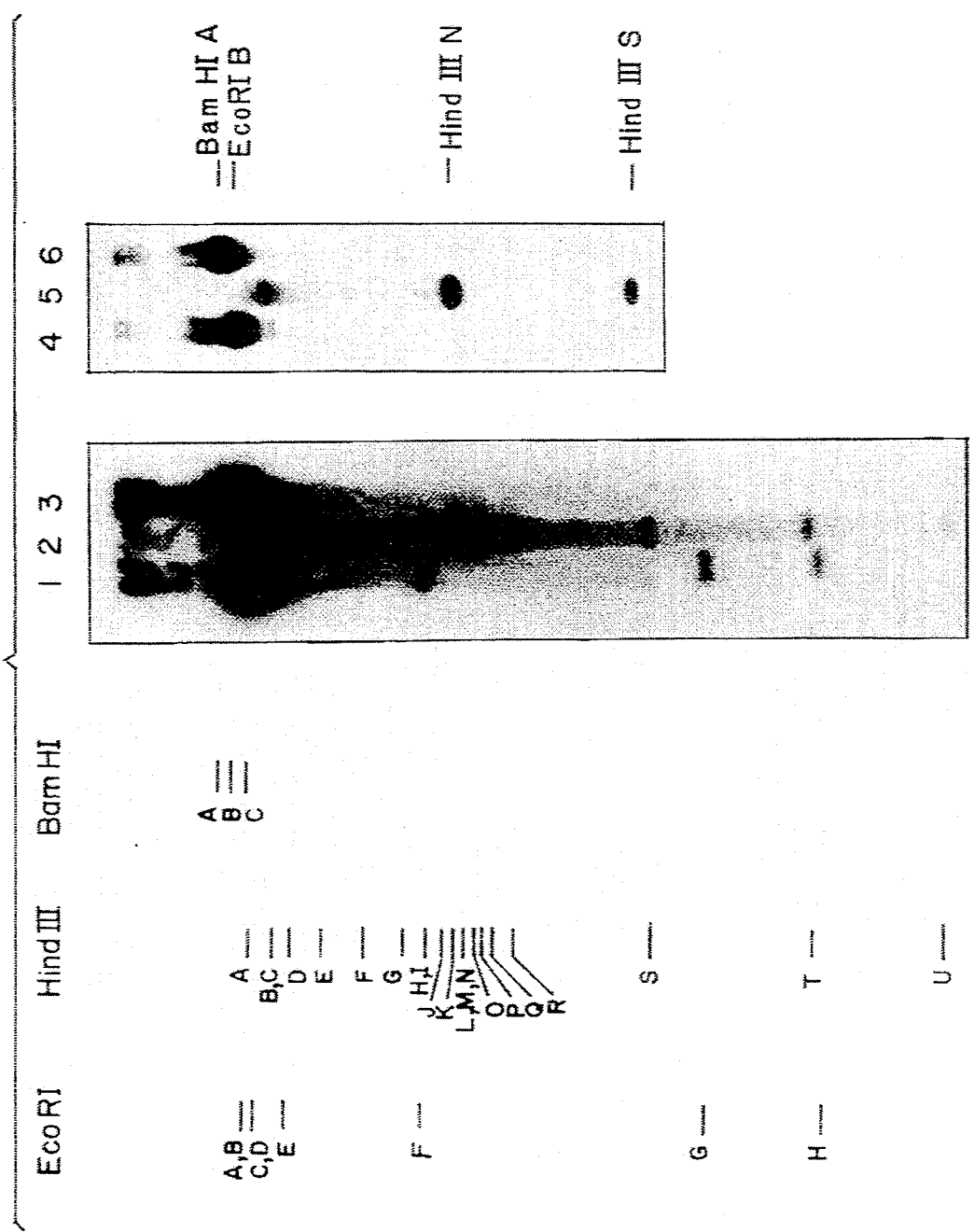

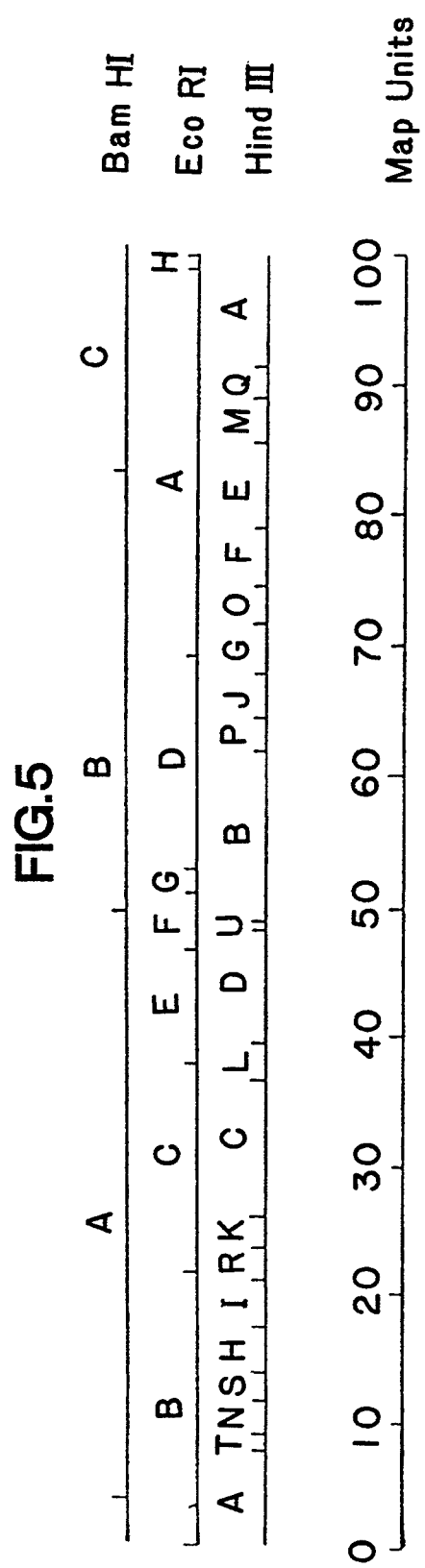

BIOLOGICAL INSECT CONTROL AGENTS AND METHODS OF USE

This invention was made with funds from the National Institutes of Health (Grant No. GE000918). The U.S. government may have certain rights this invention.

CROSS-REFERENCE TO RELATED APPLICATIONS

This application is a continuation-in-part of U.S. patent application Ser. No. 07/373,952, filed Jun. 29, 1989, now U.S. Pat. No. 5,180,581, and further claims priority from PCT US90/03758, filed Jun. 29, 1990.

TECHNICAL FIELD

The present invention relates to methods and compositions for improved biological control of insect pests. More particularly, the present invention relates to the use and manipulation of a baculovirus gene and its gene product which is effective in controlling the growth and development of insects The present invention also relates to genetically modified baculoviruses and other insect control agents that adversely affect infected insect pests.

BACKGROUND OF THE INVENTION

Interest in the biological control of insect pests has arisen as a result of disadvantages of conventional chemical pesticides. Chemical pesticides generally affect beneficial as well as nonbeneficial species. Insect pests tend to acquire resistance to such chemicals so that new insect pest populations can rapidly develop that are resistant to these pesticides. Furthermore, chemical residues pose environmental hazards and possible health concerns. Biological control presents an alternative means of pest control which can reduce dependence on chemical pesticides.

The primary strategies for biological control include the deployment of naturally-occurring organisms which are pathogenic to insects (entomopathogens) and the development of crops that are more resistant to insect pests. Approaches include the identification and characterization of insect genes or gene products which may serve as suitable targets for insect control agents, the identification and exploitation of previously unused microorganisms (including the modification of naturally-occurring nonpathogenic microorganisms to render them pathogenic to insects), the modification and refinement of currently used entomopathogens, and the development of genetically engineered crops which display greater resistance to insect pests.

Viruses that cause natural epizootic diseases within insect populations are among the entomopathogens which have been developed as biological pesticides. Baculoviruses are a large group of viruses which infect only arthropods (Miller, L. K. (1981) in *Genetic Engineering in the Plant Sciences*, N. Panopoulous, (ed.), Praeger Publ., New York, pp. 203-224; Carstens, (1980) Trends in Biochemical Science 52:107-110; Harrap and Payne (1979) in *Advances in Virus Research*, Vol. 25, Lawfer et al. (eds.), Academic Press, New York, pp. 273-355). Many baculoviruses infect insects which are pests of commercially important agricultural and forestry crops. Such baculoviruses are potentially valuable as biological control agents. Four different baculoviruses have been registered for use as insecticides by the U.S. Environmental Protection Agency. Among the advantages of baculoviruses as biological pesticides is their host specificity. Not only do baculoviruses as a group infect only arthropods, but also individual baculovirus strains usually only infect one or a few species of insects. Thus, they pose no risk to man or the environment, and can be used without adversely affecting beneficial insect species.

Baculovirus subgroups include nuclear polyhedrosis viruses (NPV), granulosis viruses (GV), and nonoccluded baculoviruses. In the occluded forms of baculoviruses, the virions (enveloped nucleocapsids) are embedded in a crystalline protein matrix. This structure, referred to as an inclusion or occlusion body, is the form found extraorganismally in nature and is responsible for spreading the infection between organisms. The characteristic feature of the NPV viruses is that many virions are embedded in each occlusion body. The NPV occlusion bodies are relatively large (up to 5 micrometers). Occlusion bodies of the GV viruses are smaller and contain a single virion each. The crystalline protein matrix of the occlusion bodies of both forms is primarily composed of a single 25,000 to 33,000 dalton polypeptide which is known as polyhedrin or granulin. Baculoviruses of the nonoccluded subgroup do not produce a polyhedrin or granulin protein, and do not form occlusion bodies.

In nature, infection is initiated when an insect ingests food contaminated with baculovirus particles, typically in the form of occlusion bodies. The occlusion bodies dissociate under the alkaline conditions of the insect midgut, releasing individual virus particles which then invade epithelial cells lining the gut. Within a host cell, the baculovirus migrates to the nucleus where replication takes place. Initially, certain specific viral proteins are produced within the infected cell via the transcription and translation of so-called "early genes." Among other functions, these proteins are required to allow replication of the viral DNA, which begins 4 to 6 hours after the virus enters the cell. Extensive viral DNA replication proceeds up to about 12 hours post-infection (pi). From about 8 to 10 hours pi, the infected cell produces large amounts of "late vital gene products." These include components of the nucleocapsid which surrounds the viral DNA during the formation of progeny virus particles. Production of the progeny virus particles begins around 12 hours pi. Initially, progeny virus migrate to the cell membrane where they acquire an envelope as they bud out from the surface of the cell. This nonoccluded virus can then infect other cells within the insect. Polyhedrin synthesis begins from 12 to 18 hours after infection and increases to very high levels by 24 hours pi. At that time, there is a decrease in the number of budded virus particles, and progeny virus are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects. (Reviewed in *The Biology of Baculoviruses*, Vol. I and II, Granados and Federici (eds.), CRC Press, Boca Raton, Fla., 1986.)

One significant disadvantage to using baculoviruses as pesticides is the length of time between virus ingestion and insect death. During this time, the pest insect continues to feed and damage crops. Because a grower is unlikely to apply the pesticide until after an infestation is apparent, it is critical that the time of feeding be minimized.

What is needed is a biological pesticide which reduces feeding by the insect before death. A biological pesticide is preferred because it creates less of an environmental hazard than a chemical pesticide. More rapid insect death is also desirable. The exploitation of (a) gene(s) that encodes (a) protein(s) which controls insect development and its incorporation into various organisms will allow improved biological control of insect pests.

SUMMARY OF THE INVENTION

In the present invention a baculovirus gene and its gene product which affect the growth, development or behavior of insects are identified. The present invention provides methods for the use of this gene and gene product, as well as methods for the inactivation of this gene or its gene product in insect control strategies. In a preferred embodiment, the egt gene encodes ecdysteroid UDP-glucosyl transferase (EGT) of AcMNPV. Expression of the baculovirus egt gene causes the production of EGT which inactivates insect molting hormones, thus preventing the insect larva from molting or pupating. Inactivation of the baculovirus egt gene allows molting and pupation of the infected larva to proceed.

The present invention encompasses a broad range of insect control agents utilizing egt genes and their gene products. The insect control agents of the present invention either cause the inappropriate synthesis of the EGT protein or prevent the normal functioning or expression of the EGT protein in the insect pest so that normal development of the insect pest is disrupted. Preferably, the organism containing the egt gene is a virus specific for the insect pest, and wherein the egt gene of the virus has been inactivated, thereby allowing the continued development of the insect host infected with the virus. Development of the insect host induces behavioral changes such as reduced feeding and, when infected by the viral pesticide, there is reduced growth and more rapid death. The present invention also includes a method for-producing the improved viral pesticide. In addition, the present invention includes a method of controlling insect pests comprising exposing the insect pest to the improved viral pesticide.

The genetically altered viruses contemplated by the present invention are more efficient pesticides than prior art viruses. Baculoviruses, such as *Autographa californica* nuclear polyhedrosis virus (AcMNPV) and *Orgyia pseudotsugata* nuclear polyhedrosis virus (OpMNPV), naturally express an egt gene whose expression prolongs the period of time an infected larva spends feeding before succumbing to the viral infection. The present invention includes inactivating the egt gene in the genome of viruses such as, but not limited to, baculoviruses. The egt gene can be inactivated by substituting in its place or inserting within it another gene such as the nonviral marker gene for B-galactosidase. It should be understood that any DNA sequence could be used to disrupt the egt gene as long as it disrupts expression of the egt coding sequence. Alternatively, all or part of the egt gene can be removed from the genome by deleting an appropriate DNA coding segment or the regulatory part of the genome that controls egt gene expression can be altered or removed. Baculoviruses with deletions inactivating the egt gene may also be produced by serial virus passage in insect cell culture. The resulting deleted viruses have the advantage that they contain no foreign DNA and differ from wild-type viruses only in that they lack a functional egt gene. Such modified baculoviruses function better as pest control agents than the viruses presently in use. As simple deletion mutants, they should also be acceptable to regulatory agencies (e.g., U.S. EPA) as genetically engineered pesticides because they do not contain heterologous DNA. Baculoviruses that do not express a functional egt gene can be modified by the insertion of genes other than egt which interfere with insect development, thus improving the efficacy of such viruses as insect control agents.

The present invention also includes a method of controlling insect pests by infecting insect larvae with a mutant virus lacking an intact egt gene or incapable of expressing a functional EGT product. The mutant virus-infected larvae attempt to molt and pupate, consequently feeding for a shorter period of time than larvae infected with wild-type or other prior art viruses. The mutant virus-infected insect larvae also die sooner than wild-type or other prior art virus-infected larvae.

It is an object of the present invention to provide a recombinant virus that is a more effective pesticide than wild-type or prior art viruses. The present invention is exemplified by the recombinant AcMNPV designated vEGTZ, in which a portion of the egt gene has been deleted and replaced by lacZ, a bacterial gene encoding β-galactosidase. Any DNA sequence which inactivates the egt gene may be substituted, as is understood by those skilled in the art. The present invention is further exemplified by the recombinant baculovirus designated vEGTDEL, in which a portion of the egt gene has been deleted. Another embodiment is a baculovirus pesticide in which the egt gene has been removed. Also included are baculoviruses in which a naturally occurring mutation, including a deletion, has resulted in the inactivation of the egt gene.

Accordingly, it is an object of the present invention to provide an egt gene and its gene product that are useful in the control of insect pests. Also within the scope of the invention are substantially purified ecdysteroid UDP-glucosyl transferase and antibody specific for it. egt genes can be identified by sequence homology to the nucleotide sequence of an egt gene in Table 1 or after determination of the EGT enzyme activity and subsequent DNA analysis. Any DNA sequence encoding an ecdysteroid UDP-glucosyl transferase is an egt gene as defined herein. An egt protein may be purified using art-known techniques and the assay procedure described in Example 4. A substantially pure egt protein preparation is one which comprises at least about 70% (w/w) ecdysteroid UDP-glucosyl transferase. A recombinant egt protein is one which has been made in any organism other than that in which the gene encoding said protein naturally occurs. The recombinant protein is expressed as a result of genetic engineering or recombinant DNA technology.

It is another object of the present invention to provide a genetically engineered virus that is an effective pesticide and is also environmentally acceptable.

It is yet another object of the present invention to provide a recombinant pesticide that lacks a functional egt gene and expresses a second gene which interferes with insect development, where the second gene is not naturally present in the organism. This second gene is one which encodes a gene product affecting ecdysis. Such a gene product can be an insect hormone which affects insect development or an enzyme which inactivates an insect hormone which regulates ecdysis. Specific examples include prothoracicotropic hormone, eclosion hormone, and juvenile hormone esterase. When genes encoding these proteins are to be incorporated into an insect virus to produce an insect control agent, that virus must be one which does not contain an egt gene or one in which an egt gene has been inactivated.

It is yet another object of the present invention to provide a genetically modified organism for use as an insect control agent that expresses a genetically inserted egt gene, where no egt gene was naturally expressed. Such genetically modified organisms expressing EGT will adversely affect insect pests, resulting in less damage to plants.

It is a further object of this invention to provide insectidal compositions suitable for agricultural application. Such compositions comprise an agriculturally suitable carrier as is understood in the art and an insect virus, such as a baculovirus, which has been genetically modified so that an egt of said virus is inactivated. Such an Egt− baculovirus may be further genetically modified to express a heterologous gene encoding an insect hormone affecting ecdysis or an enzyme which inactivates an insect hormone affecting ecdysis. Heterologous genes whose gene products affect ecdysis include, but are not limited to, prothoracicotropic hormone, eclosion hormone and juvenile hormone esterase. Preferably, insecticidal compositions comprising genetically modified baculoviruses are formulated for spray application.

Also contemplated as insecticidal compositions are those comprising an agriculturally suitable carrier and genetically modified insect parasite. An insect parasite is an organism which lives or replicates in close association with an insect larva, and has adverse affects on that larvae. An insect parasite can be a bacterium, a fungus, a virus or another insect. Such a genetically modified insect parasite comprising an egt gene will be improved as an insect control agent by the inactivation of that egt gene.

Any of the above-noted insecticidal compositions may further comprise ingredients to stimulate insect feeding. The insecticidal compositions of the present invention can be ingested by insect pests after plant application, and those insect pests susceptible to the insect control agent in the insecticidal composition will exhibit reduced feeding and will die.

It is another object of the present invention to provide a modified biological pesticide that inhibits with the expression of egt gene or with the function of its gene product.

BRIEF DESCRIPTION OF THE DRAWINGS

FIG. 1A-FIG. 1C is a schematic representation of the AcMNPV genome showing the location of the egt gene. The AcMNPV genome is presented in map units (FIG. 1A) and as EcoRI and HindIII restriction maps (FIG. 1B). FIG. 1C illustrates the restriction fragments in particular plasmids containing AcMNPV DNA.

FIG. 2A and FIG. 2B provide a schematic summary of the results from sequencing the egt gene and analyzing the sequence. FIG. 2A depicts a restriction endonuclease map of the region. The results of the computer-assisted analysis of the sequence for open reading frames are shown in FIG. 2B. The vertical lines indicate stop, codons. The sequence is "translated" in all three potential open reading frames for each DNA strands (1, 2, 3, 1′, 2′, 3′). The open reading frame (2) corresponding to egt is labeled EGT.

FIGS. 3A–3C provides a schematic representation of the structures of the egt gene regions of AcMNPV (FIG. 3A) and the recombinant viruses vEGTZ (FIG. 3B) and vEGTDEL (FIG. 3C). The hatched box represents the lacZ gene.

FIG. 4 is a schematic representation of agarose gel electrophoresis and Southern blot analysis for identification of an egt gene in the baculovirus OpMNPV.

FIG. 5 is a schematic restriction map of the OpMNPV genome.

FIG. 6 is a graph of the weight gain in control uninfected larvae or after infection of larvae at 4th instar with wt AcMNPV or vEGTZ.

FIG. 7 is a graph of larval mortality after infection of larvae at 4th instar with wt AcMNPV or vEGTZ.

FIG. 8 is a graph of the weight gain after infection of larvae at 5th instar with wt AcMNPV or vEGTZ.

FIG. 9 is a graph of larval mortality after infection of larvae at 5th instar with wt AcMNPV or vEGTZ.

FIG. 10 is a graph of larval mortality after infection of larvae at first instar with wt AcMNPV or vEGTZ at a concentration of $4.8\times10^6$ polyhedral inclusion bodies (PIB)/ml.

FIG. 11 is a graph of larval mortality after infection of larvae at first instar with wt AcMNPV or vEGTZ at a concentration of $2.4\times10^6$ PIB/ml.

DETAILED DESCRIPTION OF THE DISCLOSED EMBODIMENTS

Lepidopteran insects undergo a well characterized sequence of events during development from egg to adult insect (see *Comprehensive Insect physiology, Biochemistry and Pharmacology,* Vols. 7 and 8, Kerkut and Gilbert (eds.), Pergamon Press, Oxford, 1984 for detailed reviews). After hatching, the insect larva enters a period of extensive feeding during which time it will molt several times to allow continued growth. Stages between successive molts are known as instars. At the end of the larval growth period, the larva pupates and finally emerges as an adult insect. The processes of molting and pupation (collectively termed ecdysis) are regulated by the concerted actions of several different groups of hormones. The initial stimulus is the release of prothoracicotropic hormone (PTTH) by certain brain cells. This stimulates the prothoracic glands to produce and secrete ecydsteriods, often referred to as insect molting hormones. In the presence of juvenile hormone, a larval molt will ensue, while in the absence of juvenile hormone, the larvae will pupate. Eclosion hormone is also important in mediating several behavioral changes associated with ecdysis.

The baculovirus AcMNPV, which is used as a model system for much baculovirus research, interferes with the process of insect development discussed above in previously unsuspected manner. Insect larvae infected with AcMNPV are no longer able to molt or pupate because AcMNPV directs the synthesis of an enzyme, known as ecdysteroid UDP-glucosyl transferase (EGT), which specifically inactivates the insect ecdysteroids.

The gene encoding EGT was identified by the present inventors; it extends from 8.4 to 9.6 map units on the AcMNPV genome (FIGS. 1 and 2). As shown in Panel C of FIG. 1, viral DNA fragments encompassing the egt gene have been cloned into the plasmids pUC19, Bluescript M13+ and Bluescript M13−. FIG. 2 shows the restriction map of the egt region of the genome and the computer-assisted open reading frame analysis of the egt region. Only reading Frame 2 contains a relatively long open reading frame, which has been identified as the coding region for the egt gene. The nucleotide sequence of the egt gene and the deduced amino acid sequence of 506 amino acids are shown in Table 1. The coding sequence of egt extends from about nucleotide 149 to about nucleotide 1670.

In a preferred embodiment of the present invention, the egt gene of the baculovirus AcMNPV is inactivated by replacing a portion of the egt gene with a bacterial sequence encoding β-galactosidase. This recombinant baculovirus is designated vEGTZ. In a second preferred embodiment, part of the egt gene of AcMNPV is deleted without replacement, as shown in FIG. 3. A comparison of the proteins synthesized during wt AcMNPV and vEGTZ infection revealed that the EGT protein is a 60 kDa protein which is secreted from infected cells. An alternate mechanism for the inactivation of the insect virus egt gene is the insertion of a gene encoding an insect hormone affecting ecdysis or an enzyme which inactivates an insect hormone affecting ecdysis, which gene is expressible in an insect cell infected with said insect virus.

A search of the Genbank database revealed 21 to 22% amino acid sequence homology between egt and several mammalian UDP-glucuronosyl transferases. Homology was also found to a plant UDP-glucosyl transferase. The alignment of the egt amino acid sequence with the amino acid sequences of certain of these enzymes is displayed in Table 2.

TABLE 1

Nucleotide Sequence and Deduced Amino Acid Sequence of AcMNPV egt.

```
   1  GTCGACGCGCTTCTGCGTATAATTGCACACTAACATGTGCCCTTTGAACTTGACCTCGATTGTGTAATTTTTGGCTAT

81  AAAAAGGTCACCCTTTAAAATTTGTTACATAATCAAATTACCAGTAGTTATTCGGTTTGAAGCAAATGACTATTGTC
                                                                       egt:  M  T  I  L 161  TGCTGGCTTGCACTGCTGTCTACGCTTACTGCTGTAAATGCGGCCAATATATTGGCCGTGTTTCCTACGCCAGTTACAG
       C  W  L  A  L  L  S  T  L  T  A  V  N  A  A  N  I  L  A  V  F  P  T  P  A  Y  S 241  CCACCATATAGTGTACAAAGTGTATATTGAAGCCGTTACGGTCAAGCCCAAACTGT
       H  H  I  V  Y  K  V  Y  I  E  A  L  A  E  K  C  H  N  V  T  V  V  K  P  K  L  F 321  TTGCGTATTCAACTAAAACTTATTGCGTAATATCACGGAAATTACGGACACATGTCGTTGAGCAATACAAAAACTA
       A  Y  S  T  K  T  Y  C  G  N  I  T  E  I  N  A  D  M  S  V  E  Q  Y  K  K  L 401  GTGGCGAATTCGGCAATGTTTAGAAAGCGCGGAGTGGTGTCCGATACAGACACGGTAACCGCCGCTAACTACCTAGGCTT
       V  A  N  S  A  M  F  R  K  R  G  V  V  S  D  T  D  T  V  T  A  A  N  Y  L  G  L 481  GATTGAAATGTTCAAAGACCAGTTTGCACATATCAACGTGCGCAATCTCATTGCCAACAACCAGACGTTTGATTTAGTCG
       I  E  M  F  K  D  Q  F  D  N  I  N  V  R  N  L  I  A  N  N  Q  T  F  D  L  V  V 561  TCGTGGAAGCGTTTGCCGATTATGCGTTGGTGTTCACTTGTTTAGATCCGGCGCCCGTAATTCAAATCGCCTGGC
       V  E  A  F  A  D  Y  A  L  V  F  G  H  L  Y  D  P  A  P  V  I  Q  I  A  P  G 641  TACGGTTTGGCGGAAAACTTTGACACGGTCGGCGCCGTCGATGATGGAGGCAAACGTTGTATAAGCGGAGTGGCGAGCAA
       Y  G  L  A  E  N  F  D  T  V  G  A  V  A  R  H  P  V  H  H  P  N  I  W  R  S  N 721  TTTCGACAGGAGGCAAACGTTGGACAACAGTTTGGACCACAACACCGACAATTGAAAAACTACGCAACAAGGTGCAATTGCTTTTGCTAAAC
       F  D  T  E  A  N  V  M  T  E  M  R  L  Y  K  E  F  K  I  L  A  N  M  S  N  A 801  CGTTGCTCAAAACAGTTTGACAACAACCCGTGCCCAGCTGCGTGCAGTATCTTGGCGGAGAATCTTGTAAAGAG
       L  L  K  Q  Q  F  D  N  N  R  P  V  P  S  V  Q  Y  L  G  G  I  H  L  V  K  S 881  CTGCCATCCCATATTTGACCAAATTAAGTCCGGTCATCAACGCAAATGAACAAGTCAAAAAGCGGAACGATTTACGTAAGTTTTG
       L  H  P  I  F  D  N  N  R  P  V  P  S  V  Q  Y  L  G  G  I  H  L  V  K  S  F  G 961  GGTTGAGCATTGACACCAAATCGTTTGCAAATGAGTTTCTTTACATGTTAATCAATACGTTCAAAACGTTGGATAATTAC
       A  P  L  T  K  L  S  P  V  I  N  A  Q  M  N  K  S  K  S  G  T  I  Y  V  S  F  G 1041  ACCATATTATGGAAAATTGACGACGAAGTAGTAAAAACATAACGTTGCCGCCAACGTTAATCACGCAAATTGGTTTAA
       S  I  D  T  K  S  F  A  N  E  F  L  Y  M  L  I  N  T  F  K  T  L  D  N  Y 1121  TATTTGGAAAATTGACGACGAAGTAGTAAAAACATAACGTTGCCGCCAACGTTAATCACGCAAATTGGTTTAA
       T  I  L  W  K  I  D  D  E  V  V  K  N  I  T  L  P  A  N  V  I  T  Q  N  W  F  N 1201  TCAACGCGGCAGTTCTCATAAAAATGGCGGGTTATTACGCAAGCCGACTACAATCGAGCGACGAGGCCTTGG
       Q  R  A  V  L  R  H  K  K  M  A  A  F  I  T  Q  G  G  L  Q  S  S  D  E  A  L  E 1281  AAGCCGGGATACCCATGGTGTGTCTGCCCATGATGGGCGACCAGTTTTACCATGCGCACAATTACAGCAACTCGGCGTA
       A  G  I  P  M  V  C  L  P  M  M  G  D  Q  F  Y  H  A  H  K  L  Q  Q  L  G  V 1361  GCCCGCGCTTACCTGTTCCAGCACTGTTCCAGCGATCAACTAACGCGACGTGTTGTTTAACGCGCTAC
       A  R  A  L  D  T  V  T  V  S  S  D  Q  L  L  V  A  I  N  D  V  L  F  N  A  P  T 1441  CTACAAAAACACATGGCCGAGTTATATGCGCTCATCAATCATGATAAAGCAACGTTTCCGCCTCTAGATAAAGCCATCA
       Y  K  K  H  M  A  E  L  Y  A  L  I  N  H  D  K  A  T  F  P  P  L  D  K  A  I  K 1521  AATTCACAGAACGGTCTATTCGATATGACATGACTTCATTAAAAACAACAGTCGCCAATGTA
       F  T  E  R  V  I  R  Y  R  H  D  I  S  R  Q  L  Y  S  L  K  T  T  A  N  V 1601  CCGTATTCAAATTTCACCATTATTTACCTGGTTTTTTGAGAGGGGCTTTGTGCGACTGCGCACTTCAATTAACGTCAATA
       P  Y  S  N  Y  Y  M  Y  K  S  V  F  S  I  V  M  N  H  L  T  H  F  *

1681  AATGTTATTCCACCATTATTTACCTGGTTTTTTGAGAGGGGCTTTGTGCGACTGCGCACTTCCAGCCTTTATAAACGCTC

1761  ACCAACCAAAGCAGGTCATTATTGTGCCAGGACGTTCAAA
```

| | |
|---|---|
| EGT | MTI LCWL ALLS - - - - - TLT AVNAANI LAVFP TP AYS HHI VYKVYI EALAEKCHNVTV |
| HUMUDPGAT | Ms m. . . . ALL. . . . . . . f s s . s . g k v L- V. PT- . f S H. m. . K. . l d . L. q r . He VTV |
| MUSUDPGAT | M. . . . . . ALL. . . . . . . f . s Vk. g k v L- V. P. - . f S H. m. . Ki . l d . L. q r . He VTV |
| RATUDPGAT | M. . . . . . ALf . . . . . . . f . s . h . g k v L- V. P. - . f S H. m. . Ki . l d . L. q r . He VTV |
| | |
| EGT | VKP - KLF AYS TKTYCGNI TEI - NADMS VE- - - - - QYKKL VANS AMFRKRGVVS DTDT |
| HUMUDPGAT | l . s . . . i s f . . n s . . . . . . Ev. . . . l t . . . . . . . . . KqLV. . . A- . . . k d . . . . . . s |
| MUSUDPGAT | l r P. . . y . . . . K. . . G. . . E. . . t . v S. d . . . . . . . K. v . . . t . - . . . Rd . . . . . . . |
| RATUDPGAT | l KP. . . F. . . . K. . . d . . . EI. s t . i S. d . . . . . . . K. L. . . t . - . . . Rd . . . . . . . |
| | |
| EGT | VT AANYL GLI EMF KDQF - DNI NVRNLI ANNQ - - TFDL VVVE AF ADYAL VFGHL YDP A |
| HUMUDPGAT | . . . . . . . . f . d i l r . . . . D. v s . k k Lm. k. Q. . . FDv Vl . d Al . . f g. l l a e L. . . p |
| MUSUDPGAT | l . . . . . . . f . d . F. . . . . D. v s . k e Lmt k. Q. . . FDv l l . d p i A. . g. l i a e L. q. p |
| RATUDPGAT | i . . . . . . . f . . . y . . . . . D. v s . k q Lmt k. Q. . . FDv l . . d p i A. . g. l i a e L. h. p |
| | |
| EGT | PVI - - QI AP GYGL AENF DT VGA VAR- HP VHHP NI W- RS NFDDT E ANVMT EMRL YKEF |
| HUMUDPGAT | . V. . . r f s PGYa i . . h. g. l . . . p . . . PV. . s e l . . q . . F. e . . . Nmi - . v- LY. EF |
| MUSUDPGAT | . l . . . r f s PGY. i . . . s . g . . . . . p . . . PV. . s . l . . q . . F. e . . . Nmi - . M- LY. d F |
| RATUDPGAT | . l . . . . f s PG. . L. . . s i g . . . . . p . . . PV. . s . l . . k . . F. D. . . Nmi - . M- LY. d F |
| | |
| EGT | - - KI L- ANMS NALL KQQF GP NT P TI EKLRNKVQLLLLL NL HPI FDNNRP VPP S VQYL G |
| HUMUDPGAT | . . q l f . . k . . d . f . . e . l G. . T- Tl . . . . . K. d i . Li . . . . . Fq. . h Pl . Pn Ve f v- |
| MUSUDPGAT | . . q mf . . k . . d s f . . e . l G. . T- Tl . . . . . q . e m. Li . . n . . l e . . h P. . Pn Vd Y v- |
| RATUDPGAT | . . . . L. . k . . d t f . . e . l G. . T- Tv d . . . s KVe i . Li . . . . . l . . . h P. . Pn Vd Y i- |
| | |
| EGT | GGI HL VKS APL T KLS P VI NAQMNKS KS GTI YVS FGS S I DT KS FANEF LYMLI NTFKT |
| HUMUDPGAT | GGl H. . . a . PL. K. . . . f - . Q. s . . n g . . v f - Sl GS. v - . - n . s e E. . . . v i . s a l . . |
| MUSUDPGAT | GGl H. . . a . PL. K. . . . f - . Q. s . . . g . . v f - Sl GS. v - . - n . t e E. . . . i . . a l . . |
| RATUDPGAT | GGl H. . . a . PL. K. . . . f - . Q. s . . . g . . v f - Sl GS. v - . - n . t e E. . . . i . . a l . . |
| ZMAYUDPGAT | 285 q p . . G. . YVS FGt . . . . r p . . . El . . . L. d s . . . |
| | |
| EGT | LDNYTI LWKI DDE VVKNI TLP ANVI TQNWFNQR AVL RHKKMAAFI TQGGL QS S DEAL |
| HUMUDPGAT | i . - . . v LWr f Dg n . . . . l . L. t . l - - . kWi . Q. . l L. H. K. . AFI Th GG. n g . . . Ai |
| MUSUDPGAT | i . - . . v LWr f Dg . . . . . l . . . t . V- - . kWl . Q. . l L. H. K. . AFh Th GG. n g . . EAi |
| RATUDPGAT | i . - . . v LWr f Dg . . . . . l . . . t . V- - . kWl . Q. . l L. H. K. . AFv Th GG. n g . . EAi |
| ZMAYUDPGAT | L. . . . . . W. l . . . . l . . . a . . g . . l . . . W. . Q. AVLRH. . v g AFv Tha G. . S. . EgL |
| | |
| EGT | EAGI PMVCL PMMGDQF YHAHKL QQL GVARALDT VT VS S DQLL VAI NDVL FNAP TYKK |
| HUMUDPGAT | . p . I PMV. v Pl . a DQ. . n . . . . mk . . G. A. s LD. . TmS S. d LL. Al k . Vi - N. P. YK . |
| MUSUDPGAT | . . GI PMi . i Pl . Ge Q. . n . . . m. . . G. A. ALn . . TmS . . d v L. Al e e Vi - . . P. YKK |
| RATUDPGAT | . . GI PMi . i Pl . GDQ. . n . . . m. . . G. A. s Ln . . TmS . . d f L. Al e e Vi - d . P. YKK |
| ZMAYUDPGAT | . s Gv PM. C. P. . GDQ. . n Ar . v . h v G. G. Af e . . a mt S. . v . . Ave e l L. . . . . . r r |
| | |
| EGT | HMAEL YALI NHDKATFPP LDKAI KF TERVI RYRHDI S RQL YS L KTT AANVP YS NYYM |
| HUMUDPGAT | n . . . L- s . I h HDq p - . . PLDr A- . F. . . . v - . RH. . a k h L. . - - - A. d l . - - - . f . |
| MUSUDPGAT | n . . . L- s . I h HDq p - . . PLDr A- . F. . . . v - . RH. . a k h L. pL- - - A. Nl . - - - . f . |
| RATUDPGAT | n . . . L- s . I h HDq p - . . PLDr A- . F. . . . I - . RH. . a k h L. pL- - - A. Nl P- - - . Y. |
| ZMAYUDPGAT | . . AEL. ALv . e . . g . . . . . . K. f r F. E. V. R. * |
| | |
| EGT | YKS VFS I VMNHL THF* |
| HUMUDPGAT | Y. S- l . v . . . . La . . . . . . . . . . . . . . - . . . . . . . . . . . . . * |
| MUSUDPGAT | Y. S- l . vi . . . Ls . . . . . . . . . . . . . . . . . . . . . . . . . . . . * |
| RATUDPGAT | Y. S- l . vi . . . LT. F. . . . . . . . . . . . . . . . . . . . . . . . . . . * |

Table 2 illustrates the alignment of the egt amino acid sequence with a selection of UDP-glucuronosyl transferases and a UDP-glucosyl transferase from other species. The predicted amino acid sequence of egt is compared to human (HUMUDPGAT) (Jackson et al. (1987) Biochem. J. 242:581; mouse (MUSUDPGAT) (Kimura and Owens (1987) Eur. J. Biochem. 168:515; and rat (RATUDPGAT) (MacKenzie (1987) J. Biol. Chem. 262:9744); UDP-glucuronosyl transferases and maize UDP-glucosyl transferase (ZMAYUDPGT) (Ralston et al. (1988) Genetics 119:185), using the FASTP algorithm (Lipman and Pearson (1985) Science 227:1435), as implemented by International Biotechnologies Inc. Upper case letters denote exact matches; lower case letters denote substitutions which occur frequently among related proteins, (Dayhoff, (1978) *Atlas of Protein Sequence and Structure,* National Biomedical Research Foundation, Vol. 5, Supplement 3, Silver Spring, Md.); dots represent substitutions which occur infrequently; hyphens indicate gaps in a sequence; and a caret marks where an amino acid has been deleted from the sequence. The amino acids between the arrows are deleted from the egt gene in vEGTZ and vEGT-DEL. The homology of the AcMNPV gene to known UDP-glucose and UDP-glucuronosyl transferases supports the identification of this AcMNPV sequence as the egt coding sequence.

In mammals, the UDP-glucuronosyl transferases catalyze the transfer of glucuronic acid to a wide variety of both exogenous and endogenous lipophilic substrates (reviewed in *Glucuronidation of Drugs and Other Compounds,* Dutton (ed.), CRC Press, Boca Raton, Fla., 1986). This conjugation reaction is important in the detoxification and safe elimination of certain drugs and carcinogens. In addition, the normal metabolism and disposal of various endogenous compounds such as bilirubin and steroid hormones, proceed via conjugation with glucuronic acid. Available evidence on insect systems indicate that sugar conjugation reactions of this type involve glucose rather than glucuronic acid transfer (reviewed in Smith (1977) in *Drug Metabolism -*

*From Microb to Man*, Parke and Smith (eds.), Taylor and Francis Ltd., London, pp. 219-232). As in mammals, a wide variety of exogenous and endogenous compounds are subject to conjugation in insects.

The inventors have shown that the AcMNPV EGT protein is a UDP-glucosyl transferase which specifically conjugates glucose with ecdysteroids such as ecdysone, 20-hydroxyecdysone and makisterone A (see Table 3). Neither lysates nor extracellular medium of uninfected cells or vEGTZ-infected cells modify ecdysone. Most of the ecdysteroid glucosyl transferase activity expressed by AcMNPV-infected cells is secreted into the extracellular medium; only a relatively small level of activity is observed in AcMNPV-infected cell lysates.

Using the AcMNPV egt gene as a probe, an egt gene has been identified in another baculovirus, *Orgyia pseudotsugata* nuclear polyhedrosis virus (OpMNPV), as shown in FIG. 4. It will be recognized by those skilled in the art with the benefit of this disclosure that the egt gene of any baculovirus, insect virus or insect can be located, characterized and isolated in a similar manner to that exemplified herein. egt genes with at least 70% nucleotide sequence homology to the sequence in Table 1 are considered equivalent to the sequence in Table 1, provided those homologous genes encode an enzyme which is an ecdysteroid UDP-glucosyl transferase.

Functional equivalents of the egt gene are those which also catalyze the inactivation of ecdysteroids such as ecdysone by transferring a glucose moiety from UDP-glucose to the ecdysteroid(s). Those functional equivalents of egt may be identified using the assay methods described herein.

With the location, identification and isolation of an egt gene, the skilled artisan can inactivate that gene using the teachings of present disclosure and art-known techniques to produce a more effective insect control agent.

By comparing the properties of vEGTZ with the properties of wild-type (wt) AcMNPV, the present inventors have shown that egt expression prevents the insect from molting or pupating. Insects infected with wt AcMNPV do not molt or pupate, but insects infected with vEGTZ molt and attempt to pupate (see Table 4, in Example II).

By inhibiting molting and pupation, wt AcMNPV infection can actually prolong larval feeding time. Larvae infected at the beginning of fifth instar (the last larval instar) with wt virus continue feeding until death 5 or 6 days after infection. However, uninfected larvae stop feeding 2 to 3 days after entering fifth instar in preparation for pupation (see FIG. 8). Similar effects are observed when larvae at earlier instars are examined. Uninfected larvae cease feeding for approximately 24 hours during the molt, while larva infected by wt AcMNPV do not molt and consequently do not stop feeding (see FIG. 6).

Figure 7:
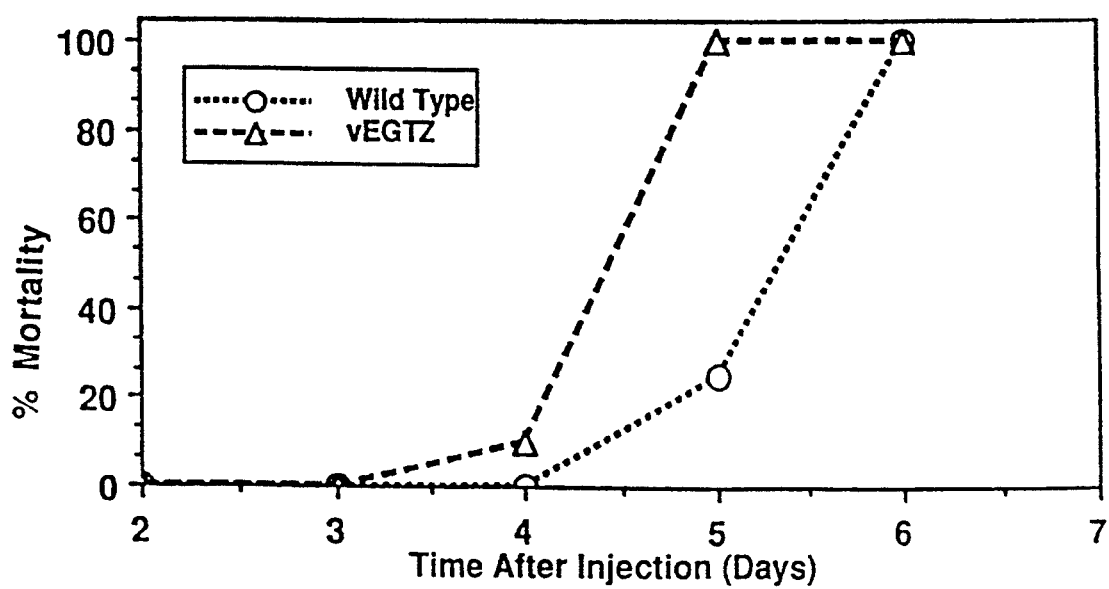
Figure 10:
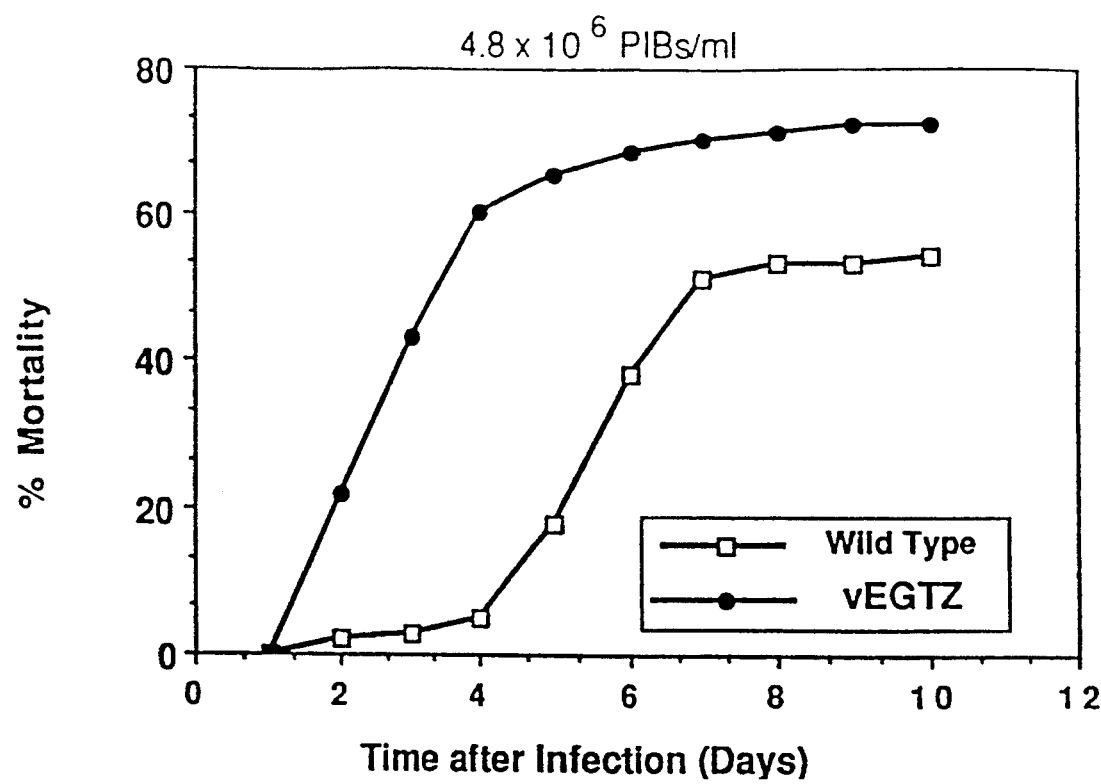
Figure 11:
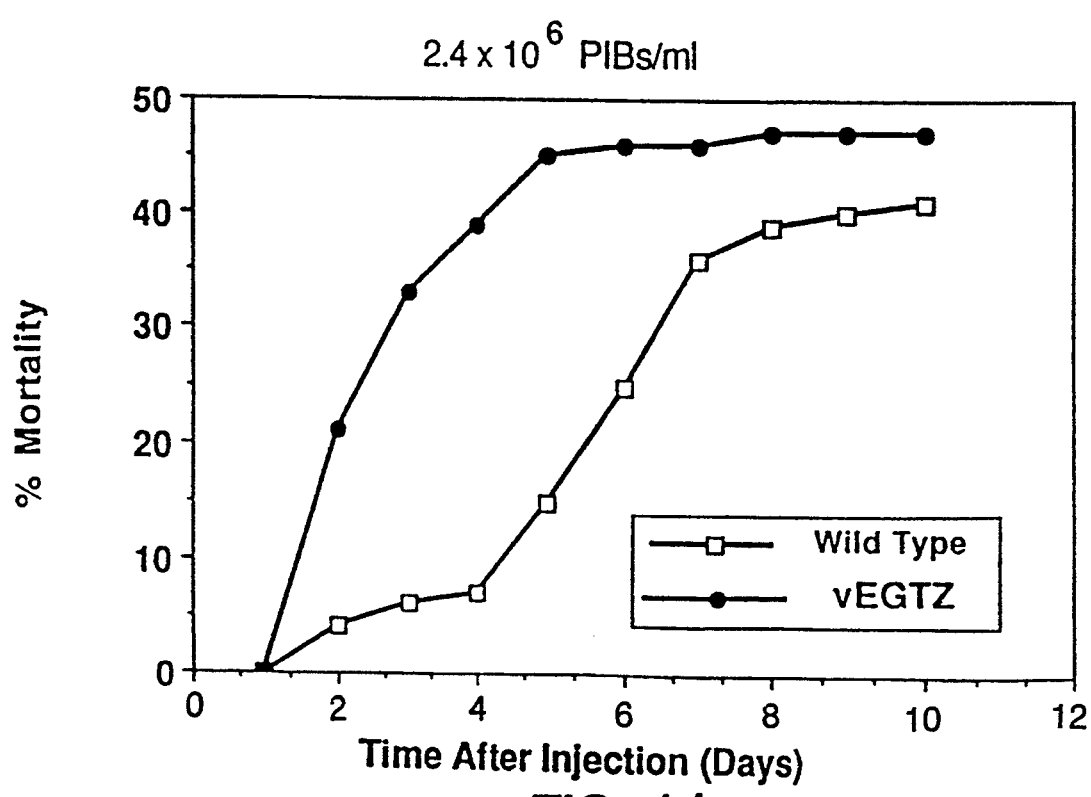

Recombinant baculoviruses which lack a functional egt gene do not prolong larval feeding time. Thus, larvae infected with vEGTZ at early fifth instar cease feeding two days after infection in preparation for pupation (see FIG. 8). However, they do not pupate and instead succumb to the viral infection even more rapidly than larvae infected with wt virus, as shown in FIG. 9. Similarly, larvae infected with vEGTZ early in fourth instar cease feeding two days after infection to molt, and then die more rapidly than wt-infected larvae (see FIGS. 6 and 7). The more rapid killing by a baculovirus lacking a functional egt gene is most dramatically seen when newly hatched first instar larvae are infected with wt AcMNPV and with vEGTZ as shown in FIGS. 10 and 11. Larvae infected with vEGTZ succumb to the viral infection 3 to 4 days sooner than larvae infected with wt AcMNPV. Therefore, recombinant baculoviruses lacking a functional egt gene are considerably more effective as insect control agents than wild-type baculoviruses. It will be apparent to those skilled in the art with the benefit of this disclosure that the egt gene can be rendered nonfunctional in any baculovirus or insect virus by any means known to the art.

The effects described above and in the following examples will be more dramatic in the field. vEGTZ-infected larvae exhibit difficulty in molting, and do so successfully only under carefully controlled laboratory conditions. When temperature and light are not rigorously controlled, many insects fail to complete the molt. These insects do not recommence feeding and die shortly thereafter.

Although the length of time progeny virus can accumulate in larvae infected with baculoviruses lacking a functional egt gene is somewhat truncated and the infected insect displays reduced growth, there is substantial production of progeny virus. The amount of virus obtained per larva following vEGTZ infection of late instar larvae is about half that obtained with wt virus. This is sufficient to allow transmission of the virus in the field and cost-effective preparation of large quantities of virus particles.

In another embodiment of the present invention, an insect virus lacking a functional egt gene is modified by genetic engineering techniques so that its effectiveness as a biological control agent is further enhanced by incorporating a second gene whose product affects insect development.

The gene encoding PTTH (a peptide hormone) can be inserted into the viral genome with the egt gene deleted and PTTH can be expressed at levels sufficiently high to affect ecdysis. Insect larvae infected with such a virus experience extreme disruption in the hormonal control of development. These insects become sick rapidly resulting in severely compromised growth and development, reduced feeding, and earlier death.

Eclosion hormone is also a small peptide hormone whose gene can be inserted into the viral genome with a nonfunctional egt gene, using techniques known to the art. Because eclosion hormone governs many behavioral changes associated with ecdysis, insects infected by an $Egt^-$ virus producing sufficiently high levels of this hormone will display behavioral and/or developmental abnormalities, such as reduced feeding.

A prime regulator of juvenile hormone titers in the insect is the enzyme juvenile hormone esterase, which inactivates juvenile hormone. A recombinant virus lacking a functional egt gene and expressing sufficiently high levels of juvenile hormone esterase can adversely affect insect behavior and/or development.

It is important to note that, while all of the above genes could be added to wild-type virus genome, they would not be expected to significantly affect insect behavior in the wild-type virus because expression of the egt gene by wild-type virus inactivates the ecdysteroid molting hormones and ecdysis is prevented, regardless of the production of other hormones. Thus, successful strategies involving the generation of viruses designed to interfere with insect ecdysis depend upon prior inactivation of the egt gene, as described in this invention.

It will be understood by those skilled in the art that mutant organisms lacking an intact egt gene or incapable of expressing a functional egt product and those which are further genetically modified so as to express another hormone modifying enzyme or a peptide hormone are included as insect control agents of the present invention.

The egt gene product has been shown to interfere with insect development in a powerful and specific manner. Ecdysteriods play a critical role in the development of essentially all insect species (reviewed in *Comprehensive Insect Physiology Biochemistry and Pharmacology*, Kerkut and Gilbert (eds.), Pergamon Press, Oxford, 1984). Thus, egt itself has considerable potential for use in broad-based insect control strategies. For example, in a fourth preferred embodiment of the present invention, crop species can be genetically engineered to constitutively produce the EGT protein by any art-known technique. Insects feeding upon such crops will be unable to complete development to adult insects, thereby providing effective long-term crop protection. Similarly, bacteria normally present in or on the plant or insect can be genetically engineered by techniques known to the art to produce the EGT enzyme. Such bacteria will likewise function as effective biological control agents.

Similarly, nonphytopathogenic, plant-colonizing bacteria may be genetically modified to express the EGT gene. Plants colonized by those genetically modified bacteria will be protected from insect pests susceptible to the action of the expressed protein(s). Nonphytopathogenic, plant-colonizing bacteria are described, for example, in U.S. Pat. No. 4,798,723, and genetic modifications of certain plant-colonizing bacteria are described in U.S. Pat. No. 4,771,131 and EPO Publication No. 0185005. Other plant-colonizing bacteria are known to the art. Any means known to the art may be used to introduce expressible genes such as those listed above to produce insect control agents.

Ingestion of such genetically modified plant material or of plant material colonized by such genetically modified plant-colonizing bacteria by a susceptible insect will result in disruption of normal development in that insect. It is known in the art that certain insects, e.g., aphids, have particularly permeable gut tissue. The skilled artisan understands the molecular biological steps necessary to construct such a plant-expressible gene and the steps necessary to incorporate such a gene into the genome of the plant.

It is likely that insects themselves express an egt gene at specific stages during their life cycle and that this constitutes an important component of the mechanisms regulating development. Thus, it is possible that an insect egt gene might be a suitable target for novel insect control strategies. The disclosure of the present invention provides the means for designing such strategies.

An additional embodiment of the present invention, ecdysteroid analogs which bind to the EGT enzyme, but which cannot be cleaved and released from the enzyme can be designed. Such "suicide substrates" will competitively bind to and inhibit or block the action of the EGT enzyme, consequently interfering with insect development. Alternatively, recombinant organisms can be genetically engineered employing teachings provided herein and as understood in the art so that expression of the insect egt gene is prevented through the production of antisense RNA, for example.

As used herein, an insect control agent is a composition or the active ingredient of a composition which has an adverse affect on insect pests. Feeding by insects is reduced in response to the insect control agent, normal insect ecdysis is disrupted and death of the insect ensues. An insect control agent of this invention can be an insect virus genetically engineered to inactivate a gene encoding an ecdysteroid modifying enzyme or one which is further engineered to express a heterologous gene encoding a protein which affects insect development, or it may be a plant, insect parasite or a nonphytopathogenic bacterium, any of which has been genetically engineered to express a heterologous gene encoding a protein which affects ecdysis.

Insecticidal compositions suitable for applications to plants to control insect pests comprise an agriculturally suitable carrier and an insect control agent. Application of an insecticidal composition of this invention can protect plants from insect pests by reducing feeding by and killing of susceptible insects.

The skilled artisan knows how to choose an insect control agent, e.g., an insect virus, which is suitable for the control of a particular insect pest.

It will be understood by those skilled in the art that the insect pests can be exposed to the insect control agent of the present invention by conventional methods including ingestion, inhalation or direct contact of the insect control agent.

Also contemplated as insect control agents are plants and entomopathogenic microorganisms which have been genetically altered to express at least one protein which affects insect development. Examples of such a protein include, but are limited to, prothoracicotropic hormone, eclosion hormone, juvenile hormone esterase and ecdipone glucosyl transferase.

Insect parasites, including bacteria viruses, fungi and other insects, can also be genetically modified to express egt. Parasitism of appropriate insects by such insect parasites will result in disruption of normal development in addition to symptomology normally associated with the unmodified parasite. The disruption of development in infected insects exacerbates the insect disease state. Feeding by and infection of the insect pest will reduce feeding and hasten death.

DNA sequences encoding an EGT protein which affect insect development disclosed herein, expressed under the regulatory control of a promoter appropriate to the organism, may be used to genetically modify an organism to produce an insect control agent. Target organisms for genetic modification include insect parasites, plants and nonphytopathogenic plant-colonizing bacteria.

The egt gene, gene product, antibodies directed against the latter, and all other reagents derived from or connected with the above are all within the scope of the present invention. The EGT protein can be substantially purified using the assay described herein and techniques known in the art.

A primary use of the genetically engineered baculoviruses of the present invention will be as components of agricultural compositions for applying to plants to effect the biological control of insect pests of plants. Many variations of preparing such agriculturally suitable compositions for insect control are known in the art.

The concentration of the insect control agent that will be required to produce insecticidally effective agricultural compositions for plant protection will depend on the type of organism and mutation used and the formulation of the composition. The insectically effective concentration of the insect control agent within the composition can readily be determined experimentally, as will be understood by the skilled artisan. For example, the insectically effective concentration of a virus can be readily determined using variations of techniques described in any of Examples VI-XI.

Agricultural compositions must be suitable for agricultural use and dispersal in fields. Generally, components of the composition must be non-phytotoxic and not detrimental to the integrity of the occluded virus. Foliar applications must not damage or injure plant leaves. In addition to appropriate solid or, more preferably, liquid carriers, agricultural compositions may include sticking and adhesive agents, emulsifying and wetting agents, but no components which deter insect feeding or any vital functions. It may also be desirable to add components which protect the insect control agent from UV inactivation. Agricultural compositions for insect pest control may also include agents which stimulate insect feeding.

Reviews describing methods of application of biological insect control agents and agricultural application are available. See, for example, Couch and Ignoffo (1981) in *Microbial Control of Pests and Plant Disease 1970-1980*, Burges (ed.), chapter 34, pp. 621-634; Corke and Rishbeth, ibid, chapter 39, pp. 717-732; Brockwell (1980) in *Methods for Evaluating Nitrogen Fixation*, Bergersen (ed.) pp. 417-488; Burton (1982) in *Biological Nitrogen Fixation Technology for Tropical Agriculture*, Graham and Harris (eds.) pp. 105-114; and Roughley (1982) ibid, pp. 115-127; *The Biology of Baculoviruses*, Vol. II, supra.

This invention is illustrated by the following examples, which are not to be construed in any way as imposing limitations on the scope thereof. It is understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The position of the egt gene on the AcMNPV genome is illustrated in FIG. 1. A scale in map units is presented above the map of the AcMNPV genome. To determine the nucleotide sequence of this gene and flanking regions, and to allow for subsequent manipulation of the gene, it is first necessary to clone several DNA fragments encompassing this region into plasmid vectors (see T. Maniatis et al. (1982) in *Molecular Cloning: a Laboratory Manual*, Cold Spring Harbor Laboratory, Cold Spring Harbor, N.Y., for standard cloning procedures). FIG. 1A shows a linear map of the AcMNPV genome after cleavage with restriction endonucleases EcoRI and HindIII. FIG. 1B is an enlargement of the genome from 7.6 to 11.1 map units showing the location of the egt gene. The original AcMNPV strain used is the L1 strain (Lee and Miller (1978) J. Virol. 27:754). The cloned DNA fragments and the names of the resultant plasmids are shown in FIG. 1C. Fragment 1, which extends from the PstI site at 7.6 mu to a BamHI site at 11.1 mu, is cloned into the plasmid vector pUC19; fragments 2 and 3 (from PstI (7.6 mu) to EcoRI (8.65 mu) and from EcoRI (8.65 mu) to SalI (10.5 mu), respectively) are both cloned into the vectors Bluescript M13+ and Bluescript M13− (Stratagene, San Diego, Calif.). Fragment 5 (BstEII (8.35 mu) to BstEII (8.7 mu) is cloned into Bluescript M13+.

A large number of subclones of BCPsE and BCES plasmids are then generated (Henikoff (1984) Gene 28:351). These subclones have progressively larger deletions of the vital insert so that they contain differing amounts of viral DNA, ranging from less than 50 base pairs to the entire vital fragment. Many of these subclones and the plasmid BCB, are then sequenced (Sanger et al. (1977) Proc. Natl. Acad. Sci. USA 74:5463) so that the entire egt gene is sequenced in both directions. The nucleotide sequences obtained are then analyzed by computer for the presence of open reading frames which can encode proteins using programs of Pustell and Kefatos (1984) Nucl. Acids Res. 12:643-655 and Devereaux et al. (1984) Nucl. Acids Res. :12:387-396. This analysis indicates that the egt gene encodes a protein of 506 amino acids. The nucleotide sequence of the egt gene and the predicted amino acid sequence of the egt gene product, are presented in Table 1.

EXAMPLE II

To construct recombinant viruses incapable of expressing a functional egt gene, further manipulation of the plasmid clones described in Example I is required. The plasmid pUCBCPsB is cleaved with restriction endonucleases EcoRI and XbaI (see FIG. 3A for sites within the egt gene) and the small fragment is discarded. The *Escherichia coli* lacZ gene, excised from pSKS104 (Casadaban et al. (1983) Methods Enzymol. 100:293-303) with EcoRI and AhaIII, is then inserted between the EcoRI and XbaI sites after the XbaI overhanging ends are filled in using T4 DNA polymerase. The resultant plasmid is designated pEGTZ. In this plasmid, the inserted lacZ gene is in frame with the preceding egt coding sequences. Alternatively, the plasmid pEGTDEL is constructed by simply ligating the EcoRI and XbaI sites together (after both sites have been blunt-ended) without inserting any sequences between them.

All viruses are derived originally from AcMNPV L-1 (Lee and Miller (1978) Supra), and are plaque-purified and propagated in the *Spodoptera frugiperda* IPLB-SF-21 cell line (SF cells) (Vaughn et al. (1977) In Vitro 13:213-217) using methods described previously (Lee and Miller (1978); Miller et al. (1986) *Genetic Engineering, Principles and Methods*, Vol. 8 (eds. J. Setlow and A. Hollaender), Plenum Press, N.Y., pp. 277-298, 1986).

The plasmid pEGTZ is then cotransfected with wt AcMNPV DNA into SF cells as described in Miller et al. (1986) supra. This procedure allows for homologous recombination to take place between sequences in the vital and plasmid DNAs, resulting in replacement of the vital egt gene with the egt-lacZ gene fusion from the plasmid. Because the remaining egt coding sequence is in frame with the lacZ sequences, such a recombinant virus will produce a fusion protein comprising the first 84 amino acids of egt joined to β-galactosidase. The recombinant virus, termed vEGTZ, can be identified because β-galactosidase expression gives rise to blue viral plaques in the presence of a chromogenic indicator such as 5-bromo-4-chloro-3-indolyl-β-D-galactopyranoside (X-gal). A diagram of the egt gene of vEGTZ is presented if FIG. 3B.

Recombinant virus vEGTDEL is obtained by co-transfecting the plasmid pEGTDEL and DNA from the virus vEGTZ into SF cells. Homologous recombination results in the replacement of the egt-lacZ fusion gene in vEGTZ with the deleted egt gene from pEGTDEL. The recombinant virus vEGTDEL is identified by its failure to form blue plaques in the presence of X-gal. The structure of the egt gene of vEGTDEL is shown in FIG. 3C.

EXAMPLE III

The product of the egt gene is identified by comparing proteins synthesized by wt AcMNPV (which makes EGT) to those produced by vEGTZ or vEGTDEL (which cannot make EGT). SF cells are infected either with wt AcMNPV or with vEGTZ at a multiplicity of infection (MOI) of 20 as described in O'Reilly and Miller (1990) J. Virol. 64:1321–1328. Uninfected cells are also analyzed. After 6 hours of infection, the cells are incubated in the presence of the radioactively labeled [$^{35}$S]-methionine for 1 hour to radioactively label all proteins made during that period. The cells are then lysed and the proteins separated by SDS-polyacrylamide gel electrophoresis (SDS-PAGE) (Laemmli et al. (1970) Nature 227:680–685). Any proteins secreted from the cells are also harvested and analyzed. After SDS-PAGE, the radiolabeled proteins are detected by autoradiography. A 60 kDa protein is secreted from wt AcMNPV-infected cells but not from vEGTZ-infected cells or uninfected cells. This 60 kDa protein cannot be detected in lysates of wt-AcMNPV infected cells, showing that it is secreted from the cell. These data demonstrate that the product of the egt gene is a 60 kDa secreted protein, properties in good agreement with the nucleotide and amino acid sequence data.

EXAMPLE IV

The enzymatic activity of the EGT protein is identified by comparing SF cells that are infected with wt AcMNPV or vEGTZ. SF cells infected with wt AcMNPV or vEGTZ are described in Example III. Twelve hours pi the cells and extracellular media are collected and processed separately. Uninfected cells are treated in parallel. Cell lysates or extracellular media are incubated in the presence of 1 mM UDP-glucose and 0.25 $\mu$Ci[$^3$H]ecdysone as described in O'Reilly and Miller (1989) Science 245:1110–1112. Ecdysteriod UDP-glucosyl transferase activity in the cell lysates or media will catalyze the transfer of glucose from the UDP-glucose to ecdysone to form an ecdysone-glucose conjugate. Ecdysone and the ecdysone-glucose conjugate are separated from one another by silica gel thin layer chromatography (Bansal and Gessner (1988) Anal. Biochem. 109:321) and visualized by autoradiography. Ecdysone-glucose conjugates (G) are only formed when wt AcMNPV-infected cell lysate or extracellular medium is assayed. No conjugates are observed when uninfected or vEGTZ-infected cell lysates or media are used, showing that the activity is due to egt expression. Most of the activity is located in the extracellular medium, in agreement with the data discussed in Example III. Proof that glucose is conjugated to ecdysone is obtained by assaying wt-infected lysates as described above except that the UDP-glucose is replaced with the radiolabeled UDP-[U-$^{14}$C]glucose. Reactions carried out with unlabeled UDP-glucose or labeled UDP-[U-$^{14}$C]glucose, with [$^3$H]ecdysone present in both reactions, and scintillation counting of the conjugate shows that both $^3$H from the ecdysone and $^{14}$C from the glucose can be detected. These data prove that the egt gene product is a UDP-glucosyl transferase which catalyses the transfer of glucose from UDP-glucose to ecdysone.

Experiments are then performed to more thoroughly investigate the substrate specificity of EGT. In these experiments various substrates (1 mM) are incubated in the presence of extracellular medium from wt-AcMNPV infected cells containing significant egt activity. As controls to ensure that any conjugation observed is due to EGT, each substrate is also incubated with media from uninfected and vEGTZ-infected cells, which cannot produce EGT. 0.05 $\mu$Ci UDP-[U-$^{14}$C]glucose are added to each reaction. Any compounds which function as substrates for EGT will be conjugated with glucose; they can be detected because the glucose is radioactively labeled.

TABLE 3

Substrate specificity of EGT

| Substrate | Mock (pmol Glucose transferred) | wild type (pmol Glucose transferred) |
|---|---|---|
| p-Aminobenzoic acid | — | — |
| Bilirubin | — | — |
| Chloramphenicol | — | — |
| Diethylstilbestrol | — | — |
| Ecdysone | — | 155.7 |
| $\beta$-Estradiol | — | — |
| 20-Hydroxyecdysone | — | 87.8 |
| Hydroxyquinoline | — | — |
| Makisterone A | — | 89.6 |
| (—) Menthol | — | — |
| Methylumbelliferol | — | — |
| $\alpha$-Napthol | — | — |
| p-Nitrophenol | — | — |
| Phenolphthalein | — | — |
| Testosterone | — | — |
| $\alpha$-Tetralol | — | — |

Substrates are incubated in the presence of medium derived from appropriately infected cells and 0.05 $\mu$Ci UDP-[U-$^{14}$C]glucose. Amounts of glucose transferred are calculated after scintillation counting of the appropriate regions of the chromatography plates.

One further control is the addition of UDP-[U-$^{14}$C]glucuronic acid to a separate set of reactions with medium from wt-infected cells to demonstrate that glucuronic acid is not transferred by this reaction. The data obtained are presented in Table 3. The only substrates identified are ecdysone, 20-hydroxyecdysone and makisterone A, all of which are ecdysteriods. No conjugation is observed using medium from mock- or vEGTZ-infected cells, confirming that the activity observed is due to expression of egt. No conjugation is observed when UDP-[U-$^{14}$C]glucuronic acid is used, demonstrating the EGT does not transfer glucuronic acid.

EXAMPLE V

To demonstrate that other baculoviruses also contain genes with substantial homology to the AcMNPV egt gene, the DNA of OpMNPV is isolated and digested separately with the restriction endonucleases EcoRI, BamHI, and HindIII. These enzyme cleave the viral DNA into several fragments of different sizes whose position in the OpMNPV genome are already known (Leisy et al. (1984) J. Virol. 52:699). Southern hybridizations are performed as described in T. Maniatis et al. (1982) supra. An internal fragment of the AcMNPV egt gene is excised from the plasmid BCES with the enzymes EcoRI and XbaI (see FIG. 1C). This fragment is radioactively labeled with $^{32}P$ and used as a probe to identify any related sequences in the OpMNPV genome. Under appropriate conditions, as understood in the art, a DNA fragment will bind to another fragment of DNA which contains sequences similar or identical to it. Thus, the AcMNPV egt probe should bind to any OpMNPV DNA fragments on the nylon membrane which contain related DNA sequences. The position of the bound probe can be visualized by exposing the membrane to X-ray film. The egt probe is first hybridized with the nylon membrane under conditions of low stringency (1 M sodium chloride, 0.3 M sodium citrate, 5% dextran sulfate, 5x Denhardt's solution, and 0.25% SDS at 37° C.). This allows the probe to hybridize to relatively distantly related sequences. The stringency of hybridization is then increased in increments, by increasing the temperature of hybridization or by adding formamide to the hybridization solution, until specifically hybridizing bands are observed. The hybridization conditions for FIG. 4 are 1 M sodium chloride, 0.3 M sodium citrate, 5% dextran sulfate, 5x Denhardt's solution, and 0.25% SDS at 68° C., for 15 h. The membrane is then washed twice for 15 min each in 0.3 M sodium chloride, 0.1 M sodium citrate, 0.1% SDS at 68° C. FIG. 4 shows that the AcMNPV egt probe binds to specific fragments of OpMNPV DNA, namely EcoRI fragment B, BamHI fragment A and HindIII fragments N and S. Note that the OpMNPV egt gene is at the same relative position in the genome as the AcMNPV gene (FIG. 5). Similar protocols can be applied for the identification of egt-homologous genes in other entomopathogens. It is understood that for highly divergent sequences, it will be necessary to confirm EGT activity using the assay method described in Example IV. Then a molecular genetic analysis of the genome will be required to isolate the gene encoding the EGT enzyme using methodology known to the art.

Alternative, the EGT gene may also be found in other organisms using the specific assay for ecdysteroid UDP-glucosyl transferase activity described in Example IV. This assay is used to identify the enzyme during purification by conventional biochemical techniques. Once purified, a partial amino acid sequence of the EGT protein is determined. This information is used to generate an oligonucleotide probe which is then used to locate the EGT gene in the genome.

EXAMPLE VI

Hemolymph titers of ecdysteroids fluctuate in a cyclic manner to regulate both larval-larval and larval-pupal molts and since glucose conjugation is suspected to inactivate ecdysteroids (Warren et al. (1986) J. Liq. Chromatogr. 9:1759; Thompson et al. (1987) Arch. Insect Biochem. Physiol. 4:1; Thompson et al. (1988) Arch. Insect Biochem. Physiol. 7:157), it is probably that egt expression during AcMNPV infection disrupts the normal developmental process of the infected insect. To demonstrate such a disruption, newly-ecdysed fourth instar *S. frugiperda* larvae are infected by injection with wt AcMNPV or vEGTZ and monitored daily for any perturbations in their development. One cohort of larvae is injected with tissue culture fluid a as negative control. The results of this experiment are presented in Table 4 below. All larvae injected with tissue culture fluid (mock-infected) molt to fifth instar as expected. Only one of sixteen larvae infected with wt virus makes this transition. In contrast, all larvae infected with the mutant vEGTZ undergo a fourth-to-fifth instar molt. Thus, egt expression by wt AcMNPV clearly and specifically inhibits host molting. Both infected groups of larvae subsequently succumb to viral infection, showing that disruption of egt does not prevent vEGTZ from killing its insect host.

TABLE 4

Inhibition of molting by AcMNPV infection.

| Virus | Molting | Mortality |
|---|---|---|
| Mock | 16 | 0 |
| Wild Type | 1 | 16 |
| vEGTZ | 16 | 16 |

Fourth instar *S. frugiperda* larvae are injected with $1 \times 10^5$ pfu wt AcMNPV or vEGTZ in 5 μl. Mock-infected larvae are injected with 5' μl tissue culture fluid. Each cohort includes 16 larvae which are maintained on artificial diet (R. L. Burton (1969) ARS publication, pp. 33–134), at 28° C. with a 14:10 hour light:dark cycle. Larvae are monitored daily for ecdysis, and mortality is recorded at day 7.

Similar results are obtained with larvae injected at early fifth instar. Using newly ecdysed fifth instar larvae, no wt-infected larvae show any signs of pupation, while the majority of vEGTZ-infected larvae display several behavioral modifications (feeding cessation, wandering, and spinning) characteristic of an impending larval-pupal molt. However, all virus-infected larvae died before pupation. These data show that AcMNPV infection prevents the insect larvae from molting or pupating. Further, the data show that this disruption of the insects' development is due to the expression of egt.

EXAMPLE VII

In vivo bioassays of wild-type (wt) AcMNPV and vEGTZ reveal that egt gene expression prolongs the time the infected larvae spend feeding and that disruption of egt improves the characteristics of the virus as a pesticide. In these studies, *S. frugiperda* larvae are injected either with wt AcMNPV or vEGTZ early in the 4th instar. For comparison, control larvae are injected with tissue culture medium containing no virus. The larvae are checked daily for weight gain, signs of molting or pupation, and mortality. The average daily weight gains of the different groups of larvae, along with the percent mortality, are plotted in FIGS. 6 and 7 respectively. Control larvae show moderate growth for the first two days. During the second day, they all molt to 5th instar. They then grow dramatically for two more days before they stop feeding in preparation for pupation. Only 1 out of 16 wt AcMNPV-infected larvae molt, and instead the larvae show continuous growth for three days following infection. At this stage, they begin to get sick, but no larvae die until day 5. All wt AcMNPV-infected larvae are dead by day 6. In contrast, all vEGTZ-infected larvae undergo a 4th to 5th instar molt and during this period, and they cease to feed. This accounts for the absence of growth from day 1 to day 2. After molting, they resume feeding but begin to show signs of sickness by day 3. They begin to die 4 days after infection and all are dead by day 5. Larvae infected with an AcMNPV derivative lacking a functional egt display reduced feeding and die more quickly post infection than those infected with wild-type AcMNPV.

Figure 8:
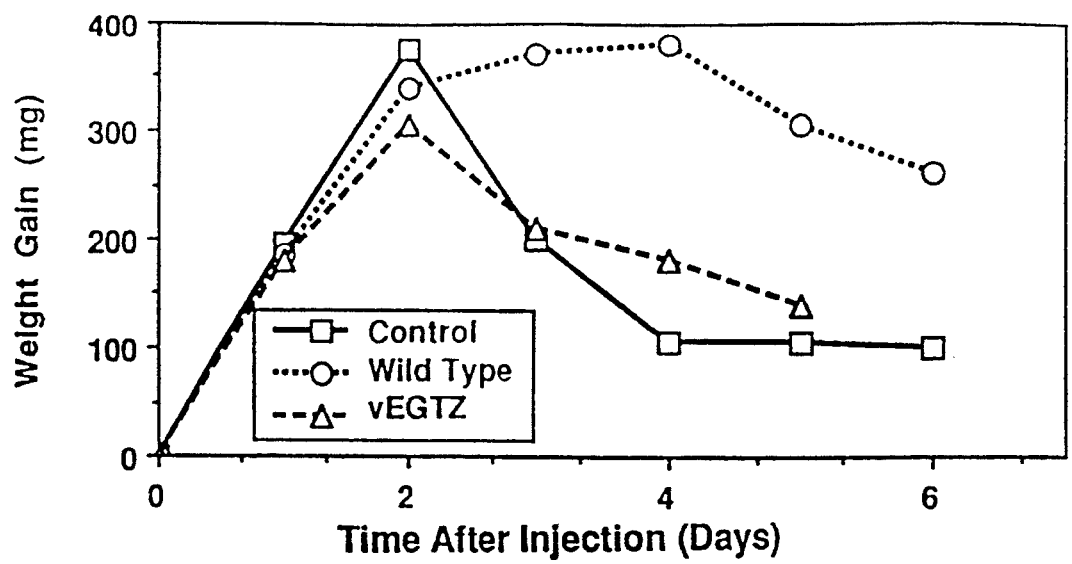
Figure 9:
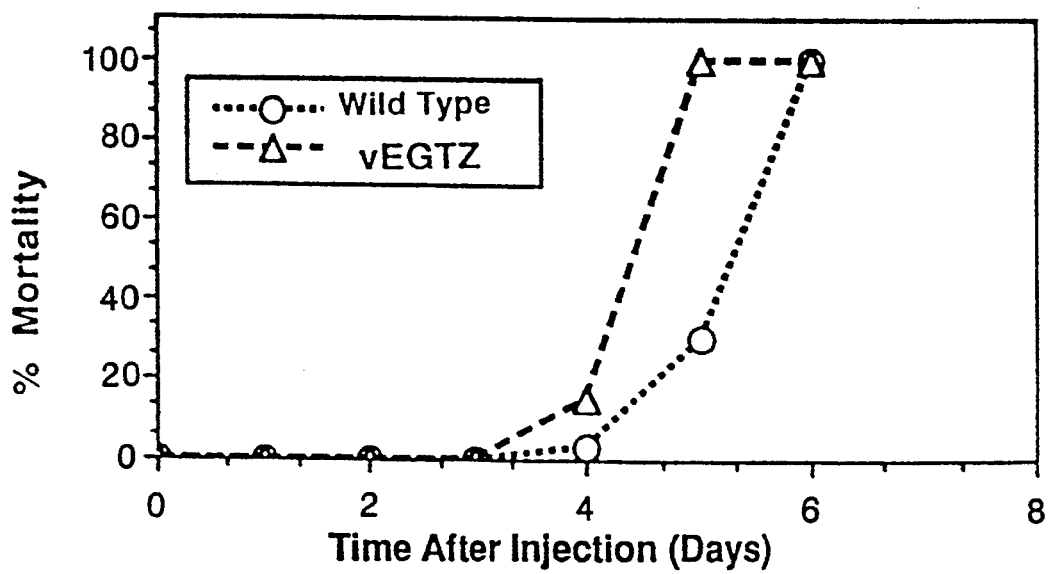

These phenomena are even more clearly observed following infection of 5th instar larvae (FIGS. 8 and 9). As expected, control larvae show considerable growth for two days before they stop feeding in preparation for pupation. This feeding cessation is accompanied by a dramatic weight loss. Wt AcMNPV-infected larvae show no signs of such a feeding cessation; they continue to feed and gain weight for two more days before they begin to get sick. Mortality is not complete until seven days after infection.

In summary, it can be seen that vEGTZ-infected larvae, like the controls, feed only for the first two days after infection. After this point, there is a dramatic weight loss as they prepare for pupation. However, none of these larvae pupate; they show signs of illness by day three and are all dead six days after infection. Again, vEGTZ infection brings about reduced feeding and earlier death.

EXAMPLE VIII

The effects of vEGTZ and wt AcMNPV infection on newly-hatched first instar S. frugiperda larvae are compared. Neonate S. frugiperda are fed a diet containing various concentrations of vEGTZ or wt AcMNPV polyhedral inclusion bodies (PIBs), and monitored daily for mortality. The results obtained for two separate doses are presented in the FIGS. 10 and 11. It can be seen that, at both doses, vEGTZ-infected larvae show considerable mortality substantially sooner than larvae infected with the wt virus. In general, larvae infected with the recombinant virus are killed between three and four days earlier than wt-infected larvae. This result provides further support that baculoviruses comprising inactivated egt genes function better as biological pesticides than wt baculoviruses with intact egt genes.

EXAMPLE IX

To construct recombinant viruses which express prothoracicotropic hormone (PTTH), the PTTH gene is cloned into the transplacement plasmid pEVmodXIV, which plasmid is described in U.S. patent application Ser. No. 07/353,847, filed May 17, 1989, which is incorporated by reference herein. This plasmid includes sequences upstream and downstream of the AcMNPV polyhedrin gene, which mediate homologous recombination of the expressible PTTH gene into the Egt$^-$ virus. A multiple cloning site is positioned at the usual site of polyhedrin translation initiation, downstream from the LSXIV-modified polyhedrin promoter (Rankin et al., Gene, 70:39 (1988)). The Bombyx mori PTTH gene is excised from the plasmid pBc22k-C19 (Kawakami et al., Science, 247:1333, (1990)) by digestion with the restriction enzyme HindIII. The HindIII cohesive ends are filled in with T4 DNA polymerase, and the plasmid then cleaved with EcoRI. pEVmodXIV is cleaved with KpnI, the KpnI overhanging end is removed with T4 DNA polymerase, and the plasmid then cleaved with EcoRI. The fragment containing the PTTH gene is cloned into the transplacement plasmid via these sites. In the resultant plasmid, pEVPTTH, the PTTH gene is located immediately downstream from the LSXIV-modified polyhedrin promoter.

Recombinant viruses expressing PTTH are obtained by cotransfecting pEVPTTH into SF cells with vEGT-DEL or wt AcMNPV DNA. Recombination between the flanking polyhedrin sequences in the viral DNA and those flanking the PTTH gene in pEVPTTH results in the replacement of the polyhedrin gene with PTTH. Viruses in which this recombination event has taken place are identified by their occlusion-negative phenotype (Miller et al., in *Genetic Engineering, Principles and Methods*, Vol. 8, J. Setlow and A. Hollaender, eds., Plenum Press N.Y., 1986, pp. 277-298). The respective recombinant viruses are designated vEGT$^-$PTTH and vWTPTTH.

The method for producing recombinant viruses expressing juvenile hormone esterase is similar. First, the *Heliothis virescens* juvenile hormone esterase gene (Hanzlik et al. (1989) *J. Biol. Chem.* 264:12419) is excised from the plasmid pJHE16B (Hammock et al. (1990) Nature 344:458) by digestion with EcoRI and KpnI. The transplacement plasmid pEVmodXIV is also cleaved with EcoRI and KpnI and the juvenile hormone esterase gene-containing fragment is inserted between these sites. pEVJHE thus includes polyhedrin gene sequences flanking the juvenile hormone esterase gene. The recombinant viruses vEGT$^-$JHE and vWTJHE are obtained by cotransfection of pEVJHE with vEGTZ or wt AcMNPV DNA, respectively, and screening for occlusion-negative plaques.

To construct recombinant viruses expressing eclosion hormone, the *Manduca sexta* eclosion hormone gene is excised from the plasmid pF5-3 (horodyski et al. (1989) *Proc. Natl. Acad. Sci. U.S.A.*, 86:8123) by digestion with EcoRI and HpaI. pEVmodXIV is cleaved with KpnI, the KpnI overhanging end removed with T4 DNA polymerase, and then cleaved with EcoRI. Insertion of the eclosion hormone gene-containing fragment into the transplacement plasmid yields the recombinant pEVEH, in which the eclosion hormone gene is positioned downstream from the LSXIV-modified polyhedrin promoter. Cotransfection of this plasmid with vEGTZ or vDA26Z DNA allows the isolation of the recombinant viruses vEGT$^-$EH and vDA26ZEH, respectively. vDA26Z is a recombinant virus with the *E. coli* lacZ gene inserted in the DA26 gene (O'Reilly et al., *J. Gen Virol*, In Press). The function of the DA26 gene is not known, and vDA26Z is phenotypically wild-type with respect to ecdysis. Because of the presence of the lacZ gene, vDA26Z derivatives give rise to blue plaques in the presence of X-gal.

EXAMPLE X

To assess the in vivo effects of these recombinant viruses, S. frugiperda larvae are injected with $2 \times 10^5$ pfu of vEGTDEL, vEGT$^-$PTTH, vWTPTTH, or both vEGT$^-$PTTH and vEGT$^-$JHE ($1 \times 10^5$ pfu each) late in 3rd instar or early in 4th instar. The daily percent mortality is presented in Table 5. For all EGT$^-$ viruses, the infected insects proceed through 4th instar and display head capsule slippage, which indicates an impending molt, by day 3. After infection by vEGT$^-$PTTH alone or by infection with vEGT$^-$PTTH and vEGT$^-$JHE together, expression of PTTH causes the infected insects to become sick rapidly, and significant mortality is observed by day 4. By contrast, insects infected with vEGTDEL do not show considerable mortality until day 5. As expected, insects infected with vWTPTTH never show signs of molting into 5th instar. No head capsule slippage is observed and the insects do not show considerable mortality until day 6. Expression of the PTTH in the absence of EGT thus advances the time of death following infection by 1 day compared to vEGTDEL. These data demonstrate the improvement of the pesticidal properties of baculoviruses by expressing genes affecting insect ecdysis, and show that egt must be inactivated for such strategies to be effective.

TABLE 5

| Virus | % Mortality | | | | | |
|---|---|---|---|---|---|---|
| | Day 3 | Day 4 | Day 5 | Day 6 | Day 7 | Day 8 |
| vEGTDEL | 4.5 | 4.5 | 68.2 | 90.9 | 90.9 | 95.5 |
| vWTPTTH | 0 | 0 | 13.0 | 39.1 | 78.3 | 95.7 |
| vEGT.pTTH | 4.2 | 62.5 | 87.5 | 100.0 | | |
| vEGT.pTTH and vEGT.JHE | 8.7 | 60.9 | 91.3 | 95.7 | 100.0 | |

EXAMPLE XI

Generation of occlusion-positive viruses which express heterologous proteins affecting insect development can be accomplished by the following scheme. First, an EGT− occlusion-negative virus expressing β-galactosidase is constructed as follows. The E. coli lacZ gene, encoding the enzyme β-galactosidase, is cloned into the transplacement vector pSynVI− described in U.S. Pat. No. 5,244,805. pSynVI− includes sequences upstream and downstream from the AcMNPV polyhedrin gene, with a multiple cloning site located immediately downstream from a synthetic modified polyhedrin promoter. The lacZ gene is excised from the plasmid pSKS105 (Casadaban et al. (1983) supra) by cleavage with PstI. The PstI overhanging end is removed with mung bean nuclease, and the plasmid cleaved with SstII. pSynVI− is cleaved with EcoRV and SstII and the lacZ gene cloned into these sites. The resultant plasmid is termed pSynVI− gal, and contains the lacZ gene immediately downstream of the synthetic modified polyhedrin promoter. pSynVI− gal is cotransfected into SF cells with vEGTDEL DNA, and occlusion-negative plaques expressing β-galactosidase are isolated, giving the virus vEGT−SynVI−gal.

To construct an occlusion-positive recombinant virus which expresses PTTH, the PTTH gene is cloned into the transplacement vector pSpXIVVI+X3.

To construct pSpXIVVI+X3, an intermediate plasmid pSpXIVVI+ is first constructed. pSpLSXIVVI+-CAT (described in U.S. Pat. No. 5,244,805) is cut with BglII and the ends filled in with DNA polymerase. Plasmid pSynVI+wtp (described U.S. Pat. No. 5,244,805) is cut with EcoRV and SacI and the small EcoRV-SacI fragment is purified. The fragments of the two plasmids are ligated and pSpXIVVI+ is selected. The pSpXIVVI+plasmid is the same as pSPLSXIV-VI+CAT except that the multicloning site from the BglII site to the SacI site is the same as that of pSyn-VI+wtp. To construct multiple cloning site #3 (described in U.S. Pat. No. 5,244,805,) a polylinker is inserted between the EcoRI-SacI sites of pSpXIVVI+. The sequence of the multicloning site in pSpXIV-VI+X3 from the fused BglII site to the SacI site is:

```
AGATCATC   GAATTCTCGAG   CTGCAGATCT   GTCGACCCGGG   AATAAA
GAGCTC
EcoRV/BglI    EcoRI—XhoI    PstI-BglII    SalI—SmaI       poly A
SacI
```

This plasmid includes an intact polyhedrin gene under the control of a wild-type polyhedrin promoter. A synthetic modified polyhedrin promoter is located upstream of, and in the orientation opposite to the polyhedrin gene. A multiple cloning site is positioned to allow insertion of genes to be expressed under the control of the synthetic modified polyhedrin promoter. The PTTH gene is excised from the plasmid pBc22k-C19 (Kawakami et al. (1990) supra) by digestion with HindIII. The HindIII overhanging end is filled in the T4 DNA polymerase and the plasmid cleaved with EcoRI. pSpXIVVI+ X3 is cleaved with EcoRI and SmaI and the PTTH gene cloned into these sites, yielding the plasmid pSpPTTH. In this plasmid, the PTTH gene is downstream from the synthetic modified polyhedrin promoter, which is located adjacent to, and in the opposite orientation to the wild-type polyhedrin promoter and coding sequences. Both the PTTH and polyhedrin genes are flanked by sequences upstream and downstream of the polyhedrin gene in AcMNPV.

pSpPTTH is cotransfected into SF cells with vEGT−SynVI−gal DNA. Recombination between the polyhedrin upstream and downstream sequences in the viral DNA and those flanking the PTTH and polyhedrin genes in pSpPTTH results in the replacement of the lacZ gene of vEGT−SynVI− gal with the PTTH and polyhedrin genes from pSpPTTH. The recombinant virus vEGT−SpPTTH is identified by an occlusion-positive, β-galactosidase-negative phenotype.

To construct an occlusion-positive virus expressing juvenile hormone esterase, the juvenile hormone esterase gene is excised from the plasmid pJHE16B (Hammock et al. (1990) supra) by digestion with KpnI, removal of the overhanging end with T4 DNA polymerase, and digestion with EcoRI. The juvenile hormone esterase gene is then cloned into the plasmid pSpXIV-VI+X3 which has been cleaved with EcoRI and SmaI. The resultant plasmid, pSpJHE, is cotransfected with vEGT−SynVI−gal DNA to generate the recombinant virus vEGT−SpJHE. This occlusion-positive virus expresses juvenile hormone esterase under the control of the synthetic modified polyedrin promoter.

Similarly, the eclosion hormone gene is excised from the plasmid pF5-3 (Horodyski et al. (1990) supra) by digestion with EcoRI and HpaI and cloned into pSpXIVVI+X3 which has been cleaved with EcoRI and SmaI. The resultant plasmid, pSpEH, is cotransfected with vEGT−SynVI−gal DNA to generate the recombinant virus vEGT−SpEH.

The occlusion-positive, EGT− viruses which are further genetically modified to express a protein affecting ecdysis (an insect peptide hormone or an enzyme which inactivates insect hormones) will reduce feeding and cause more rapid death of infected insect larvae than will wt baculoviruses or baculoviruses genetically altered only to inactivate the egt gene.

Because the insect control agents of Example XI are occluded, these viruses can be incorporated into insecticidally effective, agriculturally acceptable compositions which can be applied to infected crops. Ingestion of such occluded viral particles result in the propagation of those viruses in the field, and spread of insect control agent. Infection will cause insect death and hence, protection of the crops from insect pests.

It should be understood that the foregoing relates only to preferred specific embodiments of the present invention and that numerous modifications or alterations may be made therein without departing from the spirit and the scope of the invention as set forth in the appended claims.

We claim:

1. An insect control agent comprising a baculovirus in which a naturally occurring gene encoding an ecdysteroid modifying enzyme having ecdysteroid UDP-glucosyl transferase activity is inactivated.

2. An insecticidal composition comprising a baculovirus and an agriculturally suitable carrier, said baculovirus having been genetically modified so as to inactivate a naturally occurring gene encoding an ecdysteroid modifying enzyme having ecdysteroid UDP-glucosyl transferase activity.

3. The insecticidal composition of claim 2, wherein said baculovirus is a nuclear polyhedrosis virus.

4. The insecticidal composition of claim 3, wherein said nuclear polyhedrosis virus is selected from a group consisting of *Autographa californica* and *Orgyia pseudotsugata*.

5. A method for producing an improved insect control agent and verifying the improved characteristics of said agent, comprising:

(A) modifying a baculovirus by inactivating a gene encoding an ecdysteroid modifying enzyme having ecdysteroid UDP-glucosyl transferase activity, said gene being a natural part of the genome of said baculovirus, which step results in an improved insect control agent, and (B) verifying the improved insect control properties by a step selected form the group consisting of: confirming loss of ecdysteroid-UDP glucosyl transferase activity in insect cells infected with said modified baculovirus, confirming that an insect larva infected with said modified baculovirus experiences less weight gain than an insect larva infected with the unmodified parental baculovirus, and confirming that an insect larva infected with said modified baculovirus experiences mortality sooner than an insect larva infected with the unmodified parental baculovirus.

6. The method of claim 5, wherein said baculovirus is an *Autographa californica* nuclear polyhedrosis virus, and said modifying step comprises isolation of a virus having a deletion inactivating the gene encoding UDP-glucosyl transferase after serial passage of said *Autographa californica* nuclear polyhedrosis virus in insect cells.

7. A method for insect control comprising the step of exposing the insect to a baculovirus, wherein a naturally-occurring gene encoding an ecdysteroid modifying enzyme having ecdysteroid UDP-glucosyl transferase activity has been inactivated in said baculovirus.

8. The method of claim 7 wherein said baculovirus is selected from the group consisting of *Autographa californica* nuclear polyhedrosis virus and *Orgyia pseudotsugata* nuclear polyhedrosis virus.

* * * * *

UNITED STATES PATENT AND TRADEMARK OFFICE
CERTIFICATE OF CORRECTION

PATENT NO. : 5,352,451
DATED : October 4, 1994
INVENTOR(S) : Lois K. Miller; David R. O'Reilly It is certified that error appears in the above-indentified patent and that said Letters Patent is hereby corrected as shown below:

In column 1, line 6, insert --(Grant No. AI-23719) and with Hatch Act funding from the U.S. Department of Agriculture-- before "(Grant No. GE000918)".

In column 2, line 43, delete "vital" and replace with "viral".

Columns 11 and 12 should be headed --TABLE 2 Protein Sequence Comparison for EGT and Certain Other Steriod-Modifying Enzymes--.

In columns 11 and 12, paragraph 7, line 3 beginning with "MUSUDPGAT", following "i.-..vLW" replace "r" with --k--.

In columns 11 and 12, paragraph 7, line 4 beginning with "RATUDPGAT", following "i.-..vLW" replace "r" with --k--.

In columns 11 and 12, paragraph 8, line 5 beginning with "ZMAYUDPGAT", insert a hyphen after "Afe." and before ".amtS".

In columns 11 and 12, paragraph 9, line 3 beginning with "MUSUDPGAT", following "pL---" and before ". Nl ." replace "A" with --g--.

In columns 11 and 12, paragraph 9, line 4, insert --v-- following "n" at the front of the line.

UNITED STATES PATENT AND TRADEMARK OFFICE
CERTIFICATE OF CORRECTION

PATENT NO. : 5,352,451
DATED : October 4, 1994
INVENTOR(S) : Lois K. Miller; David R. O'Reilly It is certified that error appears in the above-indentified patent and that said Letters Patent is hereby corrected as shown below:

In columns 11 and 12, paragraph 9, line 4, following "pL---" and before ". Nl P" replace "A" with --g--.

In column 16, line 36, insert --not-- between "are" and "limited".

In column 18, lines 10, 12, 59 and 60, delete "vital" and replace with --viral--.

In column 21, line 63, delete "a as" and replace with --as a--.

In column 23, lines 36 and 37, delete "patent application Ser. No. 07/353,847, filed May 17, 1989" and replace with --Patent No. 5,244,805--.

In column 25, Table 5, the periods following "EGT" should be hypens.

Signed and Sealed this

Nineteenth Day of September, 1995

Attest:

BRUCE LEHMAN

Attesting Officer

Commissioner of Patents and Trademarks